(12) United States Patent
Neumann

(10) Patent No.: US 12,322,493 B2
(45) Date of Patent: Jun. 3, 2025

(54) SYSTEMS AND METHODS FOR GENERATING A LIFESTYLE-BASED DISEASE PREVENTION PLAN

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 828 days.

(21) Appl. No.: 17/390,237

(22) Filed: Jul. 30, 2021

(65) Prior Publication Data
US 2022/0208353 A1 Jun. 30, 2022

Related U.S. Application Data

(63) Continuation-in-part of application No. 17/136,126, filed on Dec. 29, 2020, now Pat. No. 11,139,063.

(51) Int. Cl.
| | |
|---|---|
| *G16H 20/70* | (2018.01) |
| *G06F 16/3331* | (2025.01) |
| *G06N 3/042* | (2023.01) |
| *G06N 3/08* | (2023.01) |
| *G16H 10/60* | (2018.01) |
| *G16H 40/67* | (2018.01) |

(Continued)

(52) U.S. Cl.
CPC ......... *G16H 20/70* (2018.01); *G06F 16/3331* (2019.01); *G06N 3/042* (2023.01); *G06N 3/08* (2013.01); *G16H 10/60* (2018.01); *G16H 40/67* (2018.01); *G16H 50/20* (2018.01); *G16H 70/60* (2018.01); *A61B 5/7267* (2013.01)

(58) Field of Classification Search
CPC ........ G16H 20/70; G16H 40/67; G16H 70/60; G16H 10/60; G16H 50/20; G06F 16/3331; G06N 3/042; G06N 3/08; A61B 5/7267

USPC .......................................................... 705/2–3
See application file for complete search history.

(56) References Cited

U.S. PATENT DOCUMENTS

| | | | | | |
|---|---|---|---|---|---|
| 5,692,501 | A | * | 12/1997 | Minturn | A61B 5/00 600/301 |
| 5,926,808 | A | * | 7/1999 | Evans | G06F 16/3346 707/999.005 |

(Continued)

FOREIGN PATENT DOCUMENTS

WO 2020201457 10/2020

OTHER PUBLICATIONS

Title: Dietary Quercetin Increases Colonic Microbial Diversity and Attenuates Colitis Severity in Citrobacter rodentium—Infected Mice; By: Lin; Date.

(Continued)

*Primary Examiner* — Michael Tomaszewski
(74) *Attorney, Agent, or Firm* — Caldwell Intellectual Property Law

(57) ABSTRACT

A system for generating a lifestyle-based disease prevention plan, the system including a computing device configured to receive at least a user biomarker input, produce a user profile as a function of the at least a user biomarker input, and generate a lifestyle-based disease prevention plan as a function of the user profile including training a machine learning process with a lifestyle training data set where the lifestyle training data set further comprises lifestyle elements correlated to a plurality of outputs containing diseases prevented and producing the lifestyle-based disease prevention plan as a function of the user profile and machine learning process.

20 Claims, 8 Drawing Sheets

(51) Int. Cl.
*G16H 50/20* (2018.01)
*G16H 70/60* (2018.01)
*A61B 5/00* (2006.01)

(56) References Cited

U.S. PATENT DOCUMENTS

| | | | | |
|---|---|---|---|---|
| 5,937,387 | A * | 8/1999 | Summerell | G16H 20/30 600/301 |
| 6,269,339 | B1 * | 7/2001 | Silver | G16H 20/60 600/300 |
| 6,675,159 | B1 * | 1/2004 | Lin | G06F 40/205 |
| 7,027,974 | B1 * | 4/2006 | Busch | G06F 40/253 704/4 |
| 7,044,739 | B2 * | 5/2006 | Matson | G09B 19/0092 434/127 |
| 10,357,157 | B2 * | 7/2019 | Apte | G16H 50/20 |
| 11,056,242 | B1 * | 7/2021 | Jain | G16H 10/60 |
| 2003/0233224 | A1 * | 12/2003 | Marchisio | G06F 40/211 707/E17.084 |
| 2005/0014111 | A1 * | 1/2005 | Matson | G09B 19/0092 434/187 |
| 2005/0228692 | A1 * | 10/2005 | Hodgdon | G16H 10/40 705/2 |
| 2005/0234742 | A1 * | 10/2005 | Hodgdon | G06Q 10/10 705/2 |
| 2007/0072156 | A1 * | 3/2007 | Kaufman | G16H 20/60 434/236 |
| 2007/0185391 | A1 * | 8/2007 | Morgan | A61B 5/0002 128/920 |
| 2009/0099873 | A1 * | 4/2009 | Kurple | G16H 20/60 705/3 |
| 2012/0276059 | A1 | 11/2012 | Boone | |
| 2014/0059030 | A1 * | 2/2014 | Hakkani-Tur | G06F 16/84 707/706 |
| 2014/0358890 | A1 * | 12/2014 | Chen | G06F 16/9535 707/710 |
| 2014/0372133 | A1 * | 12/2014 | Austrum | G16H 50/30 705/2 |
| 2015/0331850 | A1 * | 11/2015 | Ramish | G06F 40/40 704/9 |
| 2016/0085853 | A1 * | 3/2016 | Zelevinsky | G06F 16/338 707/765 |
| 2016/0228003 | A1 * | 8/2016 | Apte | A61B 5/0022 |
| 2016/0275073 | A1 * | 9/2016 | Poon | G06F 40/30 |
| 2017/0075891 | A1 * | 3/2017 | Bozkaya | G06F 16/243 |
| 2017/0159108 | A1 * | 6/2017 | Budding | C12Q 1/689 |
| 2017/0199189 | A1 * | 7/2017 | Wade | G16H 50/30 |
| 2018/0096111 | A1 * | 4/2018 | Wells | G16H 40/67 |
| 2018/0102190 | A1 * | 4/2018 | Hogue | G16H 10/60 |
| 2018/0260437 | A1 * | 9/2018 | Paroski | G06F 8/447 |
| 2019/0108912 | A1 * | 4/2019 | Spurlock, III | A61P 25/28 |
| 2019/0252058 | A1 * | 8/2019 | Wolf | G09B 19/0092 |
| 2019/0267140 | A1 * | 8/2019 | Segal | G16H 10/60 |
| 2020/0013488 | A1 * | 1/2020 | Lui | G01N 33/56916 |
| 2020/0073983 | A1 * | 3/2020 | Sen | G06F 16/243 |
| 2020/0138362 | A1 * | 5/2020 | Koumpan | A61B 5/486 |
| 2020/0185081 | A1 * | 6/2020 | Patel | G16H 20/90 |
| 2020/0201457 | A1 * | 6/2020 | Ko | B60K 35/50 |
| 2020/0277658 | A1 * | 9/2020 | Cutcliffe | C12Q 1/689 |
| 2020/0286623 | A1 | 9/2020 | Apte | |
| 2020/0303063 | A1 * | 9/2020 | Sharma | G16H 40/67 |
| 2020/0308627 | A1 | 10/2020 | Jain | |
| 2021/0134428 | A1 * | 5/2021 | Mason | G06F 3/1454 |
| 2021/0134429 | A1 * | 5/2021 | Mason | G16H 40/67 |
| 2021/0134433 | A1 * | 5/2021 | Burd | G16H 20/60 |
| 2022/0051665 | A1 * | 2/2022 | Bade | G06N 7/01 |
| 2022/0208353 | A1 * | 6/2022 | Neumann | G06N 20/00 |

OTHER PUBLICATIONS https://gut.bmj.com/content/69/8/1520?int_source=trendmd&int_medium=cpc&int_campaign=usage-042019; Title: Big data in IBD: big progress for clinical practice; Date: Jul. 7, 2020; By: Tabib, Nasim Sadat Seyed.

https://www.nature.com/articles/srep35216; Title: The fecal microbiota as a biomarker for disease activity in Crohn's disease; Date: Oct. 13, 2016; By: Tedjo, Danyta I.

https://www.mdpi.com/2072-6643/7/2/1282; Title: Pilot dietary intervention with heat-stabilized rice bran modulates stool microbiota and metabolites in healthy adults; Date: Feb. 16, 2015; By: Sheflin, Amy M.

https://www.ncbi.nlm.nih.gov/pmc/articles/PMC4299332/; Title: Application of metagenomics in the human gut microbiome; Date: Jan. 21, 2015; By: Wang, Wei-Lin.

* cited by examiner

SYSTEMS AND METHODS FOR GENERATING A LIFESTYLE-BASED DISEASE PREVENTION PLAN

CROSS-REFERENCE TO RELATED APPLICATIONS

This application is a continuation-in-part of Non-provisional application Ser. No. 17/136,126 filed on Dec. 29, 2020 and entitled "SYSTEMS AND METHODS FOR GENERATING A MICROBIOME BALANCE PLAN FOR PREVENTION OF BACTERIAL INFECTION," the entirety of which is incorporated herein by reference.

FIELD OF THE INVENTION

The present invention generally relates to the field of lifestyle planning for bacterial infection. In particular, the present invention is directed to systems and methods for generating a lifestyle-based disease prevention plan.

BACKGROUND

A number of possible diseases that a user may get can be predicted based on that user's biomarker, but often the disease is only treated but not prevented. Through nutrition, specific exercises, and supplement intake, such as vitamins and probiotics, a disease caused by a high number of a specific harmful microbe or low number of a beneficial microbe can be prevented.

SUMMARY OF THE DISCLOSURE

In an aspect a system for generating a lifestyle-based disease prevention plan, the system including a computing device configured to receive at least a user biomarker input, produce a user profile as a function of the at least a user biomarker input, including determining a user identifier as a function of the at least a user biomarker input, generating at least a query as a function of the user identifier, extracting at least a textual output as a function of the at least a query, and producing the user profile as a function of the at least a textual output. The computing device further configured to generate a lifestyle-based disease prevention plan as a function of the user profile including training a machine learning process with a lifestyle training data set where the lifestyle training data set further comprises a plurality of inputs containing lifestyle elements correlated to a plurality of outputs containing diseases prevented, and producing the lifestyle-based disease prevention plan as a function of the user profile and machine learning process.

In another aspect a method for generating a lifestyle-based disease prevention plan, the method including receiving, by a computing device, at least a user biomarker input, producing, by the computing device, a user profile as a function of the at least a user biomarker input, where producing the user profile includes determining a user identifier as a function of the user biomarker, generating at least a query as a function of the user identifier, extracting at least a textual output as a function of the at least a query, and producing the user profile as a function of the at least a textual out. The method further including generating, by the computing device, a lifestyle-based disease prevention plan as a function of the user profile, where generating the lifestyle-based disease prevention plan includes training a machine learning process with a lifestyle training data set where the lifestyle training data set further include plurality of inputs containing lifestyle elements correlated to a plurality of outputs containing diseases prevented, and producing the lifestyle-based disease prevention plan as a function of the user profile and machine learning process.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a lifestyle balance plan for prevention of infectious diseases. In an embodiment, a system including a computing device configured to receive at least a user biomarker input, produce a user profile as a function of the at least a biomarker input and generate a lifestyle-based disease prevention plan.

Aspects of the present disclosure can be used to help a user avoid a potential disease based on biomarker for the user by suggesting a lifestyle-based plan for the user to decrease harmful bacteria or increase beneficial bacteria in their body. Aspects of the present disclosure can also be used to predict how likely a user is of following a suggested lifestyle-based disease prevention plan and send reminders to a user when that user is likely to not follow the plan based on the prediction. This is so, at least in part, because the system trains a machine learning process with data from other users and how they followed the plan, with data being gathered from a plurality of sources, including information from a user's wearable device.

Aspects of the present disclosure allow for comparing the user lifestyle-based disease prevention plan to other users and providing the user with a chart showing how well they are following their plan as compared to other users. Exemplary embodiments illustrating aspects of the present disclosure are described below in the context of several specific examples.

Figure 1:
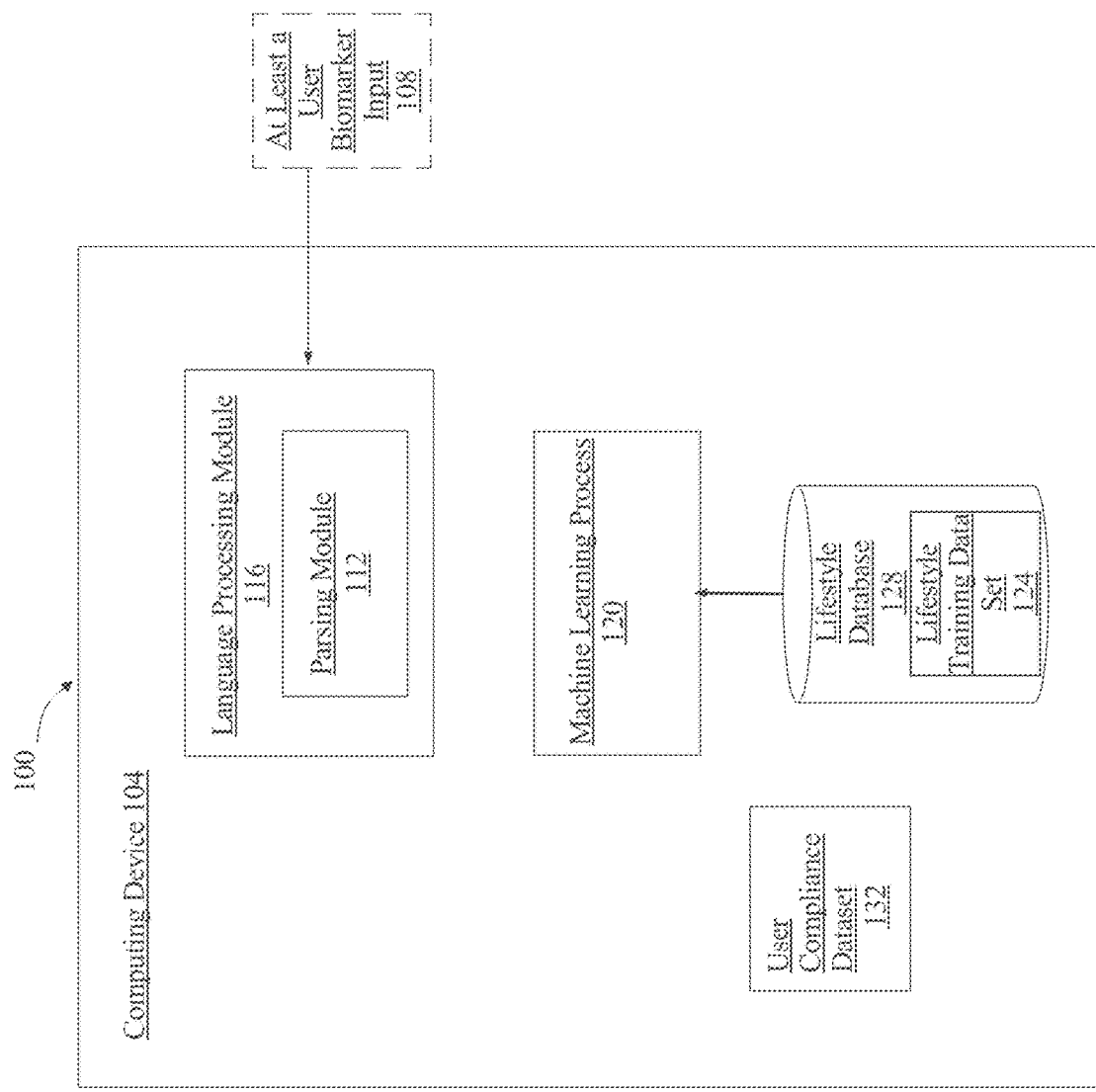
FIG. 1 is a block diagram illustrating a system for generating a lifestyle-based disease prevention plan.

Referring now to FIG. 1, an exemplary embodiment of a system 100 for lifestyle-based disease prevention plan is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive at least a user biomarker input. "Biomarker input", for the purpose of this disclosure, refers to one or more measures that of the state of a person's health, such as indicators of normal biological processes, pathogenic processes or responses to an exposure or intervention. Biomarker input may include a microbiome profile, as described above. Biomarker input may include a microbe indicator Microbe indication is described in detail throughout this disclosure. Biomarker input may include any biomarker suitable for use as a microbe indicator as described above in detail. In a nonlimiting example, biomarker input may include physiological measurements such as blood-pressure and heart rate of a user. In another nonlimiting example, biomarker input may include molecular attributes about a person such as white blood cell count, plasma, blood glucose, and the like. Biomarker input may include histological measurement such as the changes in white blood cell count, progression, or regression, of cancer cells, or other measured changes in a person's body. Biomarker input may include radiographic information such as a person's bone mineral density. Biomarker input may include a plurality of data types. Biomarker input may be in natural language, such as a document that includes a written assessment by a physician regarding a person's overall health. Biomarker input may also include a person's current alimentary diet. In a nonlimiting example, a user's biomarker input may include the user's blood pressure, microbial composition in the body, white blood cell count, changes in white blood cell count based on measurements over a period of time, and many other attributes that allows for creating a lifestyle-based disease prevention plan. In an embodiment, a biomarker input may include information collected from a user, such as by a questionnaire and/or an input from a device operated by a user.

Continuing to refer to FIG. 1, computing device 104 is configured to produce a user profile as a function of the at least a user biomarker, where producing the user profile include determining a user identifier as a function of the at least a user biomarker input, generating at least a query as a function of the user identifier, extracting at least a textual output as a function of the at least a query, and producing the user profile as a function of the at least a textual output. User identifier, as used for the purpose of this disclosure, includes any information contained in the biomarker input that identifies the person that the information pertains to. In a nonlimiting example, a user identifier may be the user's name, but also multiple other identification data used throughout the documents included in the biomarker input, such as a document that uses an alphanumerical unique identifier to refer to the patient instead of the patient's name.

Still referring to FIG. 1. In an embodiment, generating the at least a query as a function of the user identifier may include using a parsing module 112. At least a query, as used in this disclosure, is at least a datum used to retrieve text that will be incorporated in at least a textual output, where retrieval may be affected by inputting the at least a query into a data structure, database, and/or model, and receiving a corresponding output as a result, for example as set forth in further detail below. At least a textual output as used in this disclosure, includes an output that includes alphanumerical characters in any natural language. At least a textual output may also include commonly used symbols, or medical abbreviations, such as symbols that are used to describe "greater/lesser than", equal signs, arrows describing increases/decreases, and the like. Parsing module 112 may generate at least a query by extracting one or more words or phrases from the input, and/or analyzing one or more words or phrases; extraction and/or analysis may include tokenization, in relation to a language processing module 116. A language processing module 116 may generate the language processing model by any suitable method, including, without limitation, a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs, as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 116 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 1, parsing module 112 may utilize, incorporate, or be a language processing module 116 as described above. Language processing module 116 may be configured to map at least a user input to at least a query, using any process as described above for a language processing module 116. Extraction and/or analysis may further involve polarity classification, in which parsing module 112 may determine, for instance, whether a phrase or sentence is a negation of the semantic content thereof, or a positive recitation of the semantic content; as a non-limiting example, polarity classification may enable parsing module 112 to determine that "my feet hurt" has a divergent meaning, or the opposite meaning, of the phrase "my feet don't hurt." Polarity classification may be performed, without limitation, by consultation of a database of words that negate sentences, and/or geometrically within a vector space, where a negation of a given phrase may be distant from the non-negated version of the same phrase according to norms such as cosine similarity.

Continuing to refer to FIG. 1, parsing module 112 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 112 may perform algorithms for named entity recognition. Named entity recognition may include a process whereby names of users, names of informed advisors such as doctors, medical professionals, coaches, trainers, family members or the like, addresses, place names, entity names, or the like are identified; this may be performed, without limitation, by searching for words and/or phrases in user database. For instance, parsing module 112 may identify at least a phrase, which may include one or more words, map the at least a phrase to at least a query element, and then assemble a query using the at least a query element. Mapping at least a phrase to at least a query element may be performed using any language processing technique described in this disclosure, including vector similarity techniques.

With continued reference to FIG. 1, parsing module 112 may extract and/or analyze one or more words or phrases by performing dependency parsing processes; a dependency parsing process may be a process whereby parsing module 112 and/or a language processing module 116 communicating with and/or incorporated in parsing module 112 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 112 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasami-Younger (CKY), Earley algorithm or Chart parsing algorithms. Disambiguation may alternatively or additionally be performed by comparison to representations of syntactic structures of similar phrases as detected using vector similarity, by reference to machine-learning algorithms and/or modules, or the like.

Still referring to FIG. 1, parsing module 112 may combine separately analyzed elements from at least a user input together to form a single query; elements may include words, phrases, sentences, or the like, as described above. For instance, two elements may have closely related meanings as detected using vector similarity or the like; as a further non-limiting example, a first element may be determined to modify and/or have a syntactic dependency on a second element, using dependency analysis or similar processes as described above. Combination into a query may include, without limitation, concatenation. Alternatively, or additionally, parsing module 112 may detect two or more queries in a single user input of at least a user input; for instance, parsing module 112 may extract a conversational query and an informational query from a single user input. An informational query, as used in this disclosure, is a query used to retrieve one or more elements of factual information; one or more elements may include, without limitation, any data suitable for use as a prognostic label, an ameliorative process label, and/or biological extraction data as described above. One or more elements may include an identity of a category of a prognostic label, ameliorative process label, biological extraction datum, informed advisor, or the like. One or more elements may include an identity of any factual element, including an identity of a place, person, informed advisor, user, entity, or the like. A conversational query, as used herein, is a query used to generate a textual response and/or response form, such as an overall sentence structure, templates, words, and/or phrases such as those usable for entries in narrative language database as described above, for inclusion of information returned in response to an informational query, for a response to a question, comment, phrase, or sentence that is not in itself a request for information, and/or for a request for clarification and/or more information as described in further detail below. A conversational query may include one or more pattern-matching elements, such as regular expressions, "wildcards," or the like.

With continued reference to FIG. 1, parsing module 112 may be configured to convert at least a query into at least a canonical or standard form of query; for instance, and without limitation, once a query has been detected, parsing module 112 may convert it to a highly closely related query based on vector similarity, where the highly closely related query is labeled as a standard form or canonical query. In an embodiment, converting to a standard form query may enable more efficient processing of queries as described below, as a reduced space of potential queries may be used to retrieve conversational and/or informational responses.

Still referring to FIG. 1, computing device 104 is configured to generate a lifestyle-based disease prevention plan as a function of the user profile, where generating the user profile includes training a machine learning process with a lifestyle training data set where the lifestyle training data set further comprises a plurality of inputs containing lifestyle elements correlated to a plurality of outputs containing diseases prevented, and producing the lifestyle-based disease prevention plan as a function of the user profile and machine-learning process. Lifestyle-based disease prevention plan as used in this disclosure includes a plan created for the user that has the goal of improving the persons health through a plurality of methods, such as specific nutritional recommendations, suggested exercise schedules, suggested intake in probiotics, suggested intake of vitamins, and other methods of improving a persons' health based on a lifestyle followed by the person. In a nonlimiting example, based on the biomarker input of a user, the lifestyle-based disease prevention plan may create a plan for the user that suggests a set periodic intake of specific probiotic based on a person's microbiome profile, also schedules specific exercises that will ensure the person is staying healthy while not pushing themselves above a point that the system determines to be unhealthy based on the person's biomarker input. In a nonlimiting example, the lifestyle-based disease prevention plan may suggest a specific diet for a person based on the white and red blood cell count for that person and may also suggest an intake of calcium supplements based on a persons measured bone density included in the biomarker input. "Lifestyle elements" as used herein refer to any aspects of a lifestyle such as amount of exercise, nutritional intake, probiotics intake, sleep pattern, mental health, vitamin supplement intake, and so on. Lifestyle training data may be from a plurality of sources such as publicly accessible websites, American College of Lifestyle Medicine, other users' lifestyle-based disease prevention plans, simulated lifestyle-based disease prevention plans, and the like. Lifestyle training data set may include any training data set included in this disclosure. Lifestyle training data set may be stored in and accessed from a Lifestyle database. In an embodiment, the lifestyle-based disease prevention plan may include a microbiome balance plan. "Microbiome balance plan" is described above, and further below, in this disclosure.

Still referring to FIG. 1, in one embodiment, training a machine learning process may include utilizing a neural network. Neural network is described in detail further below.

Alternatively, or additionally, and still referring to FIG. 1. In one embodiment, computing device 104 may monitor a user for compliance with the lifestyle-based disease prevention plan. In one embodiment, computing device 104 may monitor a user compliance with the lifestyle-based disease prevention plan by receiving information from a wearable device. In one embodiment, computing device 104 may be configured to send the user a reminder related to the lifestyle-based disease prevention plan. In a non-limiting example, computing device 104 may monitor a user's exercise pattern through a wearable device to check if the user is following the lifestyle-based disease prevention plan and send a reminder to the user with steps needed to be back on track. A wearable device includes any device, worn by a person or attached to a person's body, that takes a measurement of a user's body. A wearable device may contain a sensor. In a nonlimiting example, a wearable device may be a smartwatch. In another nonlimiting example, wearable device may be a subcutaneous implant.

Alternatively, or additionally, computing device 104 may be configured to generate a user compliance dataset. In one embodiment, computing device 104 may send the user a lifestyle-based disease prevention comparison set based on the user compliance dataset. In some embodiments, computing device 104 may train a machine learning process with the user compliance dataset. In some embodiments, computing device 104 may predict the likeability of a user of following the lifestyle-based disease prevention plan based on the machine learning process trained with the user compliance dataset. In one embodiment, computing device 104 may send the user periodical reminders as a result of a predicted likeability of a user following the lifestyle-based disease prevention plan. In a nonlimiting example, the computing device 104 may use a given population compliance results to train a machine learning model and predict, based on that model, how likely a given population is of following the plan, if a low likeability is predicted the computing device may send reminders to users related to their lifestyle-based disease prevention plan. In an embodiment, the computing device includes attributes specific to AI assistant software in the transmission of the reminders. In a nonlimiting example, system may include an app that includes an AI assistant, such as the API.ai owned by Expert Systems Enterprises located at 6110 Executive Boulevard, Suite 690, Rockville, MD 20852, where the transmission includes attributes that allow for the seamless incorporation of the reminders into automated tasks, such as voice reminders to a user at the times set related to the contents of the reminder.

Figure 2:
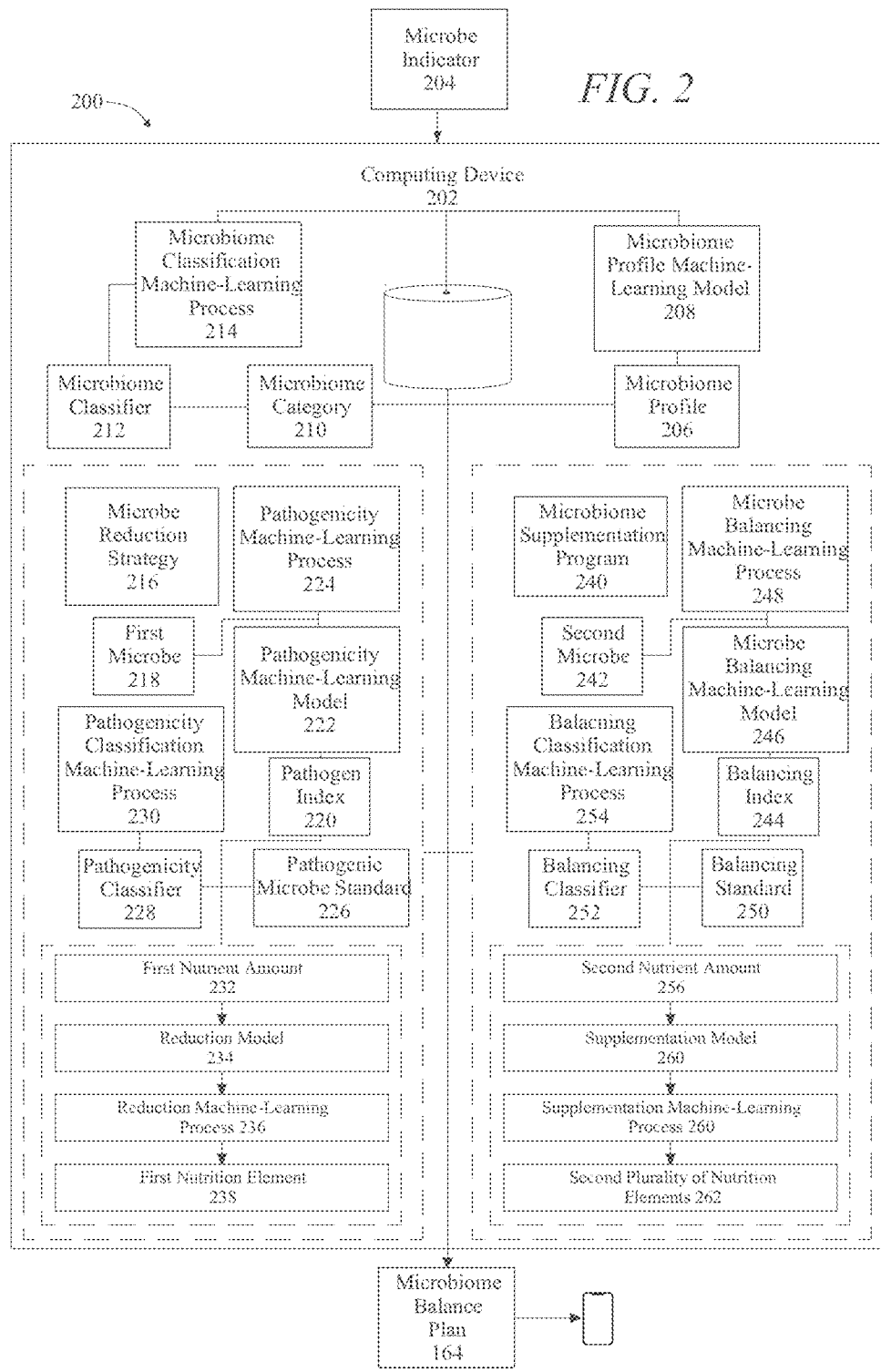
FIG. 2 is a block diagram illustrating a system for generating a microbiome balance plan for prevention of bacterial infection.

Referring now to FIG. 2, computing device 104 is configured to receive at least a microbe indicator. A "microbe indicator," as used in this disclosure, is a biological and/or chemical substance or process that is indicative of a relationship between the microbiome and the body. A "microbiome," as used in this disclosure, is a heterogeneous or homogenous aggregate of microorganisms and their associated products that reside on or within a user. A "microorganism," as used in this disclosure, is a microscopic non-human organism. A microorganism may include a bacterium, archaea, fungi, protist, virus, amoeba, parasite, spore, egg, larvae, and the like, that may reside in within or on a body. A microorganism may be simply referred to as a "microbe". Microorganisms may include microbes with populations supported in and/or colonizing biofluids, tissues, on the skin, epithelia of organs, cavities of the body, and the like. For instance and without limitation, the human microbiome may include microorganisms that reside on or within the skin, mammary glands, placenta, seminal fluid, uterus, ovarian follicles, lung, saliva, oral mucosa, conjunctiva, biliary tract, and gastrointestinal tract. Human microbiome may include colonization by many microorganisms; it is estimated is that the average human body is inhabited by ten times as many non-human cells as human cells, some studies estimate that ratio as 3:1, or even 1:1. Some microorganisms that colonize humans are commensal, meaning they may co-exist without harm; others have a mutualistic relationship with their hosts, such as a metabolic symbiosis where microbes improve digestion, whereas the host provides a niche. Conversely, some non-pathogenic microorganisms may harm human hosts via the metabolites they produce, like trimethylamine, which the human body converts to trimethylamine N-oxide via FMO3-mediated oxidation. Microbes that are expected to be present, and that under normal circumstances do not cause disease, may be deemed 'normal flora' or 'normal microbiota'.

Continuing in reference to FIG. 2, microbiome indicator 208 may include analysis of molecules from a biological extraction of a user. A biological extraction may include an analysis of a physical example of a user, such as a stool sample, DNA sequencing, and the like Microbe indicator 204 may include measurements of the presence of microorganisms, such as culturing results relating to microorganisms (bacteria culturing, viral plaque assays, and the like). Microbe indicator 204 may include diagnostic results such as Enterotube™ II results, metabolic profiling, genetic sequence (e.g., using targeted PCR probe-based microbiome profiling), biochip and/or sensor-based microbiome profiling (e.g., immobilizing macromolecules to a microarray, and the like). Receiving the at least a microbe indicator 204 may include receiving a result of one or more tests relating to the user and/or analysis of one or more tests. For instance and without limitation, an analysis of a biological extraction such as a blood panel test, lipid panel, genomic sequencing, and the like. Such data may be received and/or identified as a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 2, microbe indicator 204 may include test results of screening and/or early detection of infection, diagnostic procedures, prognostic indicators from other diagnoses, from predictors identified in a medical history, and information relating to biomolecules associated with the user such as the presence of and/or concentrations of: BBA68, BBA64, BBA74, BBK32, V1sEC6, BBA15, BBB19, BB032, BBA24, BB0147, CRP, IL-6, PCT, Serum Amyloid A (SAA), ESR, sTREM-1, ANP, PSP, IL-8, 11-27, suPAR, and the like. Microbe indicator 204 may include diagnostics, for instance the use of a K—OH (potassium hydroxide) test for the presence of fungal spores, catalase test, coagulase test, microscopy methods (e.g., wet mounts, Gram staining, and the like), ELISA tests, antigen-antibody tests, and the like.

Continuing in reference to FIG. 2, microbe indicator 204 may include DNA sequencing data. For instance, sequencing of 16S ribosomal RNA (rRNA) among microbial species. Such data may include "next-gen", or "second-generation" sequencing technologies with incomplete and variable sequences obtained, for instance, from stool samples. There exist a multitude of nucleic acid primer sequences used for determining the presence of microbiota species, with individual species resolution, and 1,000's+ organismal throughout. Such primers may include DNA primers for reverse-transcription PCR (rtPCR) to generate cDNA libraries from RNA templates. In such an example, microbe indicator 204 may include the RNA sample and its analysis by rtPCR. Microbe indicator 204 may include any PCR experimentation analysis (e.g., qPCR, RT-qPCR, host start PCR, and the like) that may be used to amplify microorganism nucleic acid and detect the presence of and identify microorganisms. Microbe indicator 204 may include data relating to the presence and/or concentration of products relating from a microorganism (e.g., toxins, metabolic waste products, LPS, and the like). Microbe indicator 204 may include data relating to the presence and/or concentration of products relating from infection by a microorganism (e.g., blood serum proteins, complement, antibodies, T-cell activation, and the like).

Continuing in reference to FIG. 2, microbe indicator 204 may include culturing techniques used to support growth of a population of microorganisms isolated from a user to identify and measure the population size of microorganism. Microbe indicator 204 may include analysis of growth on selective media (e.g., to select for the presence of a microorganism such as EMB, MacConkey, and the like), differential media (e.g., to distinguish between species, such as blood agar, chocolate agar, and the like), Kirby-Bauer antibiotic sensitivity test, among other assays regarding growth, isolation, and characterization of microorganisms originating from a user. Microbe indicator 204 may include biochemical analysis of microbial products such as the presence of bacterial spores such as *Bacillus* spp. spores in the gut.

Continuing in reference to FIG. 2, microbe indicator 204 may include results enumerating the identification of mutations in nucleic acid sequences. Microbe indicator 204 may include the presents of single nucleotide polymorphisms (SNPs) in genetic sequences. Microbe indicator 204 may include epigenetic factors, such as non-heritable alterations to genetic information. Microbe indicator 204 may include genetic and epigenetic factors for the user, for instance as a user may have mutations and/or SNPs in lactate dehydrogenase, or its gene/enzyme regulation, as it relates to symptomology relating to lactose intolerance. Microbe indicator 204 may include genetic and epigenetic factors for microbes originating from a user, for instance the presence of mutations regarding to antibiotic-resistance (e.g., inheriting R-factors, mutation in 30S/50S rRNA leading to rifampicin resistance, and the like).

Continuing in reference to FIG. 2, computing device 202 may receive microbe indicator 204 as user input. User input may be received via a "graphical user interface," which as used is this disclosure, is a form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction such as replying to health state questionnaire for symptomology onboarding, uploading a genetic sequencing file, hyperlinking a medical history document, and the like) with a user device. A person skilled in the art, having the benefit of the entirety of this disclosure, will be aware of various additional test data, biomarker data, analysis, and the like, that may be received as microbe indicator data and how system may receive such data as input.

Continuing in reference to FIG. 2, microbe indicator 204 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 2, microbe indicator 208 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module, as described in further detail below, to produce outputs given data provided as inputs; this is in contrast to a non-machine learning software programing where the commands to be executed are determined in advance by a subject and written in a programming language.

Continuing in reference to FIG. 2, microbe indicator 204 may be organized into training data sets and stored and/or retrieved by computing device 104, without limitation, as a relational database, a key-value retrieval database such as a NOSQL database, or any other format or structure for use as a database that a person skilled in the art may recognize as suitable upon review of the entirety of this disclosure. Microbe indicator 204 training data may alternatively or additionally be implemented using a distributed data storage protocol and/or data structure, such as a distributed hash table and the like. Microbe indicator 204 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of microbe indicators may be stored, retrieved, organized, and/or reflect data and/or records as used herein, as well as categories and/or populations of data consistent with this disclosure.

Continuing in reference to FIG. 2, computing device 104 is configured to retrieve a microbiome profile related to the user. A "microbiome profile," as used in this disclosure, is a profile that includes at least a metric relating to a plurality of microbes as a function of the at least a microbe indicator 204. Microbiome profile 206 may include any number of current microbial colonization state determinations including 'past infections', 'vaccinations', 'antibiotics taken', 'surgeries' (e.g., appendectomy, adenoidectomy, and the like), and the like. Microbiome profile 206 may include the identification of microorganism family, genus, species, strain, serotypes, and the like. Microbiome profile 206 may include data represented by strings, numerical values, mathematical expressions, functions, matrices, vectors, and the like. Microbiome profile 206 may include a plurality of metrics and their relationships to a plurality of microbes as a function of the at least a microbe indicator 204, such as the presence of and degree of colonization of bacteria isolates.

Continuing in reference to FIG. 2, microbiome profile 206 may include qualitative determinations, such as binary "yes"/"no" determinations for harboring a bacterial species, pathogen, antibiotic resistant strain, "normal"/"abnormal" determinations about the presence of and/or concentration of microbe indicators 204, for instance as compared to a normalized threshold value of a biomarker among a subset of healthy adults. Microbiome profile 206 may include mathematical representations of the current state of the microbiome and bacterial infection, such as a function describing, for instance, the risk of developing infection as a function of time. Such representations of microbiome profile 206 may allow for determinations such as instantaneous infection risk, such as daily, weekly, monthly, and the like, risks. A "bacterial infection," as used in this disclosure, is an illness, imbalance, condition, malady, disorder, complaint, affliction, problem and the like caused by bacteria. A bacterial infection may include a disease such as strep throat due to bacteria such as *Streptococcus pyogenes*. A bacterial infection may include a disease such as cellulitis due to bacteria such as *Staphylococcus aureus*. A bacterial infection may be located on any part of the body and/or throughout the body. For instance and without limitation, a bacterial infection such as a urinary tract infection may be contained to the urinary tract of a user, while a bacterial infection such as sepsis may be widespread in the bloodstream of a user.

Continuing in reference to FIG. 2, retrieving microbiome profile 206 may include a process of searching for, locating, and returning microbiome profile 206 data. For example, microbiome profile 206 may be retrieved as documentation on a computer to be viewed or modified such as files in a directory, database, and the like. In non-limiting illustrative embodiments, computing device 104 may locate and download microbiome profile 206 via a web browser and the Internet, receive as input via a software application and a user device, and the like Still referring to FIG. 2, computing device 104 may retrieve microbiome profile 206 from a database. Database may be implemented, without limitation, as a relational database, a key-value retrieval database such as a NOSQL database, or any other format or structure for use as a database that a person skilled in the art would, upon the benefit of this disclosure in its entirety, may recognize as suitable upon review of the entirety of this disclosure. Database may include a microbiome database, as described in further detail below. Alternatively or additionally, database may be implemented using a distributed data storage protocol and/or data structure, such as a distributed hash table and the like. Database may include a plurality of data entries and/or records, as described herein. Data entries for microbe profile 206 may be flagged with or linked to one or more additional elements of information, which may be reflected in data entry cells and/or in linked tables such as tables related by one or more indices in a relational database.

Continuing in reference to FIG. 2, retrieving microbiome profile 206 may include training a microbiome profile machine-learning model with training data that includes a plurality of data entries wherein each entry correlates microbe indicators 204 to a plurality of microorganisms and generating the microbiome profile 206 as a function of the microbiome profile machine-learning model and the at least a microbe indicator 204. Correlating microbial indicators 208 to a plurality of microorganisms may include deriving relationships between microbe indicator(s) 204 as they relate to the identification of and or quantification of microorganism populations in the user. Such a process may include threshold values, for instance biomarker cutoffs for determining that a user may be harboring a microorganism, for comparing microbe indicator 204. Such training data may include data such as cytokine levels, genes expression levels, white blood cell levels, and metabolites correlated to microorganism identities according to what the levels may be, combinations of levels, level cutoffs, and the like.

Continuing in reference to FIG. 2, microbiome profile machine-learning model 208 may include any machine-learning algorithm such as K-nearest neighbors' algorithm, a lazy naïve Bayes algorithm, and the like, any machine-learning process such as supervised machine-learning, unsupervised machine-learning, or the like, or any machine-learning method such as neural nets, deep learning, and the like, as described in further detail below. Microbiome profile machine-learning model 208 may be trained to derive an algorithm, function, series of equations, or any mathematical operation, relationship, or heuristic, that can automatedly accept an input of microbe indicator(s) 208 and assign a numerical value to and generate an output of microbiome profile 206. Microbiome profile machine-learning model 208 may derive individual functions describing unique relationships observed from the training data for each microbe indicator 204, wherein different relationships may emerge between users and user cohorts such as subsets of alike users, healthy users, obese users, 18-25 yrs. old, among others. Computing device 104 may generate the microbiome profile 206 as a function of the microbiome profile machine-learning model 208 and the at least a microbe indicator 204 (input). Microbiome profile 206 include any number of parameters.

Continuing in reference to FIG. 2, training data for microbiome profile machine-learning model 208 may include results from biological extraction samples, health state questionnaires regarding symptomology, medical histories, physician assessments, lab work, and the like. Microbiome profile training data may originate from the subject, for instance via a questionnaire and a user interface with computing device 104 to provide medical history data, nutritional input, food intolerances, and the like Computing device 104 may receive training data for training microbiome profile machine-learning model 208. Receiving such training data may include receiving whole genome sequencing, gene expression patterns, and the like, for instance as provided by a genomic sequencing entity, hospital, database, the Internet, and the like Microbiome profile training data may include raw data values recorded and transmitted to computing device 104 via a wearable device such as a bioimpedance device, ECG/EKG/EEG monitor, physiological sensors, blood pressure monitor, blood sugar and volatile organic compound (VOC) monitor, and the like. Microbiome profile training data may originate from an individual other than user, including for instance a physician, lab technician, nurse, caretaker, and the like. It is important to note that training data for machine-learning processes, algorithms, and/or models used herein may originate from any source described for microbiome profile training data.

Continuing in reference to FIG. 2, in non-limiting illustrative examples, the expression levels of a variety of isolates from human stool samples such as bacterial species identifications, sequencing data, and the like, which may be retrieved from a database, such as a repository of peer-reviewed research (e.g. National Center for Biotechnology Information as part of the United States National Library of Medicine), and the trained microbiome profile machine-learning model 208 derived function(s) may calculate an average and statistical evaluation (mean±S.D.) from the data, across which the user's microbe indicators 204 are compared. In such an example, microbiome profile machine-learning model 208 may derive a scoring function that includes a relationship for how to arrive at a solution according to the user's microbe indicator (e.g., number of mRNA transcripts presence in stool) as it relates to the presence of a microorganism. In this way, computing device 104 may use the trained microbiome profile machine-learning model 208 to "learn" how identify and enumerate all microorganisms that may relate to the user. Microbiome profile 206 may become increasingly more complete, and more robust, with larger sets of microbe indicators 204.

Continuing in reference to FIG. 2, computing device 104 is configured to assign the microbiome profile 206 to a microbe category. A "microbe category," as used in this disclosure, is a determination about a current microbial colonization state of the user according to a classification of the user as a function of a subset of users. Microbe category 210 may include tissue or organ type classification, such as "skin infection", "gum infection", and the like Microbe category 210 may include a microorganism species, identifier, or groping such as "*Enterococcus*", "*Clostridium* spp." and the like Microbe category 210 may include a designation about antibiotic resistance, such as "MRSA" (methicillin-resistant *Staph aureus*), "VREs" (vancomycin-resistant *Enterococcus*), and the like Microbe category 210 may include a designation regarding a type of bodily dysfunction that may involve a particular microorganism, or lack thereof, "dairy intolerance", "celiac disease", "puffy adenoids", "allergic reaction", and the like Microbe category 210 may include a predictive classification, where a user does not currently have a bacterial infection but may include data that indicates a microbe category 210 with which the user may be most closely categorized to, such as for 'imminent infection'. For instance, a medical history of ear infections may classify an individual into categorizations concerning microorganisms that cause middle ear infections, such as "*Streptococcus pneumoniae* (pneumococcus)", "*Hemophilus influenzae*", "*Pseudomonas*", "*Moraxella*", and the like, microbe category 210, despite not currently having ear infection. Microbiome profile 206 may have associated with it an identifier, such as a label, that corresponds to a microbe category 210, series of microorganism identities, and the like Continuing in reference to FIG. 2, assigning microbiome profile 206 to microbe category 210 may include training a microbiome classifier using a microbiome classification machine-learning process and training data which includes a plurality of data entries of microbiome profile data from subsets of categorized users. Microbiome classification machine-learning process may generate microbiome classifier using training data. Training data may include bacterial species, microbe biomarkers 208, and the like, correlated to data entries that may be recognized as microbe categories 220. Training data may originate from any source as described above. A "microbiome classifier" may include a machine-learning model, such as a mathematical model, neural net, or program generated by a machine learning algorithm known as a "classification algorithm," as described in further detail below. Microbiome classifier 212 may sort inputs (such as the data in the microbiome profile 206) into categories or bins of data (such as classifying the data into a microbe category 210), outputting the bins of data and/or labels associated therewith. In non-limiting illustrative examples, training data used for such a classifier may include a set of microbe indicators 204 as it relates to classes of bacterial infections, symptoms, bacterial species, and the like. For instance, training data may include ranges of user biological extraction values as they may relate to the variety of infections.

Continuing in reference to FIG. 2, microbiome classification machine-learning process 214 may include any classification machine-learning algorithm which may be performed by machine-learning module, as described in further detail below. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a microbiome classifier may classify elements of training data to elements that characterizes a sub-population, such as a subset of microbe indicator 204 (e.g., bacterial isolates as it relates to a variety of microbiome categories 220) and/or other analyzed items and/or phenomena for which a subset of training data may be selected. In this way, microbiome classifier.

Continuing in reference to FIG. 2, computing device may classify the microbiome profile 206 to the microbe category 210 using the microbiome classifier 212 and assigning the microbe category 210 as a function of the classifying. For instance and without limitation, training data may include sets of microbe indicators 204 correlated to bacterial infection types, species, tissues, and the like, as described above. Microbiome classification machine-learning process 214 may be trained with training data to "learn" how to categorize a user's microbiome profile 206 as a function of trends gene expression, SNPs, bacterial isolates, user symptomology, and the like. Such training data may originate from a variety of sources, for instance from user input via a health state questionnaire and a graphical user interface. Training data may originate from a biological extraction test result such as genetic sequencing from user stool samples, blood panel for metabolites, and the like Training data may originate from a user's medical history, a wearable device, a family history of disease, and the like. Training data may similarly originate from any source, as described above, for microbe indicator 204 and determining microbiome profile 206. In this way, microbe classifier 224 may be free to "learn" how to generate new microbe categories 220 derived from relationships observed in training data.

Continuing in reference to FIG. 2, classification using microbiome classifier 212 may include identifying which set of categories (microbe category 210) an observation (microbiome profile 206) belongs. Classification may include clustering based on pattern recognition, wherein the presence of microbe indicators 204, such as bacterial species, genetic indicators, symptoms, and the like, identified in microbiome profile 206 relate to a particular microbe category 210. Such classification methods may include binary classification, where the microbiome profile 206 is simply matched to each existing microbe category 210 and sorted into a category based on a "yes"/"no" match. Classification may include weighting, scoring, or otherwise assigning a numerical valuation to data elements in microbiome profile 206 as it relates to each microbe category 210. Such a score may represent a likelihood, probability, or other statistical identifier that relates to the classification into microbe category 210, where the highest score may be selected depending on the definition of "highest".

Continuing in reference to FIG. 2, computing device 104 is configured to determine, using the microbe category 210 and the microbiome profile 206, a microbe reduction strategy. A "microbe reduction strategy," as used in this disclosure, is a strategy including at least a nutrient amount intended to be taken by the user to reduce the population of a microorganism. A "nutrient amount," as used in this disclosure, is a numerical value(s) relating to the amount of a nutrient. A "nutrient," as used in this disclosure, is any biologically active compound whose consumption is intended to have an effect on the microbiome. Reducing the population of a microorganism may include slowing the growth rate, undoing colonization, depleting the population, suppressing growth by supporting competing microorganisms, among other strategies.

Continuing in reference to FIG. 2, determining a microbe reduction strategy 216 includes identifying at least a first microbe 218 to be eliminated from microbiome profile 206, wherein identifying at least a first microbe 218 may include generating a pathogen index. A "first microbe," as used in this disclosure, is at least one microorganism, microorganism type, or the like, that was identified to be removed from microbiome profile 206. A "pathogen index," as used in this disclosure, is a systematic index used to classify a microorganism as a pathogen. Pathogen index 220 may include a scoring index, repository, listing, and the like, of microbes (bacteria, protists, yeasts, and the like) that represent pathogens for user. Pathogens may be user-specific (one isolate may represent a pathogen for a particular user, but not another). Pathogens may include microbes' part of an active infection of the user. Pathogens may include microbes that have colonized user and not part of an ongoing infection and are not invading tissue. Pathogens may include opportunistic pathogens, or microbes that may be part of microbiome profile that may cause imminent disease in the user if provided the opportunity.

Continuing in reference to FIG. 2, generating a pathogen index may include training a pathogenicity machine-learning model using a pathogenicity machine-learning process and training data which includes a plurality of data entries of microbiome profile data from subsets of users correlated to indexing values for identifying pathogenic microbes. Pathogenicity machine-learning model 222 may include any machine-learning algorithm, model, and the like, as described in further detail below. Pathogenicity machine-learning process 224 may include any machine-learning process, algorithm, or the like, as performed by a machine-learning module described below. Training data for generating pathogen index 220 may originate from any place as described herein, and may include data relating the severity of symptoms, amount of organism needed to establish infection (IC50, LD50, and the like), relating to a plurality of microorganisms. Such training data may be used to train pathogenicity machine-learning model 222 to derive an index, such as a scoring function, for assigning "pathogenicity" to a plurality of microbes. Such an index may include numerical values, "pathogen"/"non-pathogen" designations, and the like Such a trained machine-learning model may extrapolate a pathogenicity index based on similarity of species, for instance in non-limiting illustrative examples, a user may harbor varying isolates of *Clostridium* spp., where *C. difficile*, *C. botulinum*, and *C. tetani* may have pathogenicity indexes due to prevalence of disease, vaccination, and study, whereas the pathogenicity index variety of *Clostridium*, or even Firmicutes, commensal isolates may be extrapolated, as they relate to pathogens. Pathogen index 220 may be determined from a subset of alike users, where pathogenicity machine-learning model 222 may be trained with training data that includes thousands of user's microbiome organisms as it relates to symptomology, medical history, and the like Such data may be generated by a classifier, where subsets of data are used to train pathogenicity machine-learning model 222 to identify pathogen identities, and assign indexing values as a function of pathogen severity, pathogen incidence, and the like In this way pathogenicity machine-learning model 222 may identify microorganisms that are uniquely pathogenic, according to user; alternatively or additionally, pathogenicity machine-learning model 222 may also identify infection and/or colonization in a user that was not previously identified.

Continuing reference to FIG. 2, computing device 202 may assign the pathogen index 220 to each element in the microbiome profile 206 of the user according to the pathogen index 220 and the pathogenicity machine-learning model 222. If pathogen is identified, it may be labeled for "microbe reduction plan." This may be done using a mathematical operation, such as subtraction. For instance and without limitation, microbes may be assigned a pathogen index numerical value, wherein microorganisms are provided values on a [0, 100] index based on pathogenicity, or propensity to cause infection, likelihood to be found in healthy subsets of users, and the like Microorganisms identified as pathogens may thus retain higher values according to a cutoff threshold, for instance values >60 are considered pathogenic. In such an instance, computing device 104 may subtract each datum in microbiome profile, wherein each datum may be assigned a pathogen index, from a microbiome profile average according to a subset of healthy users. This may result in low scores, or potentially zeros, in places where a beneficial pathogen was matched up to microbiome profile, such as a pathogen-to-pathogen comparison via pairwise alignment, resulting in the positive identification of a pathogen. Similar negative selection process(es) for pathogens may be performed. Such a "subset of healthy users," may include controls for age such as +/−5 years of user current age, fitness level for instance only in users who exercise regularly, body mass index (e.g., only users >10 BMI, and <25 BMI), and the like This may be performed to identify potential sources of bacterial infection more accurately and/or to locate potentially beneficial isolates lacking from user microbiome.

Continuing in reference to FIG. 2, identifying at least a first microbe 218 may include generating a pathogenic microbiome standard, wherein generating the pathogenic microbiome standard may include training a pathogenicity classifier using a pathogenicity classification machine-learning process and training data which includes a plurality of data entries of microbiome profile data from subsets of users correlated to microbe categories based on pathogenicity. A "pathogenic microbe standard," as used in this disclosure, is a microbiome reference that is used to measure microbiome pathogenicity. A pathogenic microbe standard 226 may include a listing of microbiome organisms that may be found in particular subsets of users. A particular "subset of users" for a pathogenic microbe standard 226 may include users that are alike or different from user, categorized based on sex, fitness level, diet, age, medical history, diagnoses, symptoms, among other categorizations based on microbe indicator 204, microbiome profile 206, microbe category 210, among other categorizations. Data relating to microbes present in users may be classified using pathogenicity classifier 228. Pathogenicity classifier 228 may include any classifier as described herein. Pathogenicity classification machine-learning process 230 may include any machine-learning process, algorithm, and the like, as performed by machine-learning module in further detail below.

Continuing in reference to FIG. 2, training data for pathogenicity classifier 228 may include microbiome profile 206 data of a plurality of users correlated to microbe categories based on pathogenicity. Training data may include any data entries, data types, and/or data arrangements as described herein. Training data may originate from any source as described herein. Training data may include a plurality of microbiome profile data from a plurality of users correlated to pathogenic microbes in the plurality of users. In non-limiting illustrative examples, pathogenicity classifier 228 may be trained with a plurality of data entries that correlate microbes, which have been indexed according to pathogenicity using pathogen index 220 among healthy adults, so that outliers may be more easily identified. Outliers may represent novel bacterial isolates, new bacterial strains, rare commensal isolates, public health risks, and the like. Pathogenicity classifier 228 trained in such a manner may identify patterns in the training data the assist in classification of microbes based on propensity to cause infection. This way, computing device 104 may automatedly accept a user's microbiome profile 206 as an input and use pathogenicity classier 256 to derive how to identify true pathogens more accurately according to pathogenic microbiome standard 256.

Continuing in reference to FIG. 2, identifying at least a first microbe 218 may include determining a pathogenicity threshold from the pathogenic microbiome standard 226. A "pathogenicity threshold," as used in this disclosure, is a cutoff threshold determined from the pathogen index 220 and the pathogenic microbiome standard 226 for comparing microbiome profile(s) 212 for identifying pathogen microorganisms. For instance and without limitation, pathogenicity threshold may include a numerical value, function of values, mathematical expression, and the like which indicates a value, above which a microorganism may be identified as a pathogenic microbe that represents a first microbe 218 to be eliminated. In non-limiting illustrative examples, pathogenicity threshold may include a tiered numerical value system, wherein pathogenicity threshold dictates that microbes with pathogenicity index <20 are non-pathogenic and >75 should be eliminated. Pathogenicity threshold may be determined from pathogenicity classifier 228 according to observations about the incidence rate of microbes in health cohorts.

Continuing in reference to FIG. 2, identifying the at least a first microbe 218 may include comparing the microbiome profile 206 of the user to the pathogenicity threshold. Pathogenicity threshold may be generated as a function of the pathogenic microbiome standard 256 and the pathogenicity classifier 228. Computing device 104 may compare microbiome profile 206 and pathogenicity threshold identify microorganisms that correlate to infection and/or represent pathogenic organisms. Computing device 104 may compare microbiome profile 206 and pathogenic microbiome standard 256 by comparing the strings representing organism identities between lists to identify microbes that match, wherein organisms that match will be added to microbiome reduction strategy 232. Computing device 104 may compare a pathogen-indexed microbiome profile 206 to pathogenicity threshold, pathogen index 220, or pathogenic microbiome standard 256, to identify pathogens. A "pathogen indexed microbiome profile," as used in this disclosure, is a microbiome profile 206 of a user that has been indexed according to pathogen index 220 for comparing to pathogenicity threshold. For instance, if an organism exists in microbiome profile 206 that does not match pathogenic microbiome standard 256 computing device may derive a pathogenicity solution according to scoring criteria derived from the pathogen index 220 and the pathogenicity threshold.

Continuing in reference to FIG. 2, identifying the at least a first microbe 218 may include identifying the at least a first microbe 218 as a function of the comparison. Computing device 104 may compare microbiome profile 206 and pathogenic microbiome standard by determining a pathogenic threshold value. For instance and without limitation the comparison may include a threshold numerical value, above which a microorganism is identified as a pathogen. In such an instance, a threshold value may be derived from the pathogenicity classifier 228, wherein a minimal pathogen index 220 value is identified, as microbiomes are classified according to prevalence among a cohort of users (e.g., among healthy adults, and the like).

Continuing in reference to FIG. 2, determining a microbe reduction strategy 216 includes determining at least a first nutrient amount that aids in reduction of the at least a first microbe 218. First microbe 218 may include a microbe identified as a function of locating opportunistic pathogenicity potential, digestive issues, for instance using microbiome indicator(s) 208. A "first nutrient amount," as used in this disclosure, is a quantity of a nutrient amount intended to reduce the population of a first microbe 218. A first nutrient amount 232 may include a mass amount of a vitamin, mineral, macronutrient (carbohydrate, protein, fat), a numerical value of calories, mass amounts of phytonutrients, antioxidants, bioactive ingredients, probiotics, active cultures, nutraceuticals, and the like.

Continuing in reference to FIG. 2, determining at least a first nutrient amount that aids in reduction of the at least a first microbe 218 may include training a reduction model using a reduction machine-learning process and training data, wherein training data includes a plurality of data entries of nutrition amounts correlated to reducing microbial populations. A "reduction model," as used in this disclosure, is a machine-learning model that may be trained to determine nutrient amounts that may reduce populations of a pathogenic microorganism. Reduction machine-learning process 236 may include any machine-learning process, algorithm, and/or model as performed by a machine-learning model described in further detail below. Reduction machine-learning process 236 may include, for instance using a machine-learning process and/or method (e.g., supervised learning) to train a machine-learning model (e.g., neural net, naïve Bayes algorithm, and the like) with training data that includes a plurality of data entries that correlate nutrients amounts to pathogen colonization. Training data for reduction model 234 may include a plurality of data that includes food items, supplements, probiotics, and the like as they may relate to growth rates, CFU/mL, selectively pressure, and the like, for microorganisms. Such training data may originate from any source described herein; for instance, peer-reviewed research may include data that describes effects on microbiome health from consuming a variety of products such as animal products, organic vs non-organic fruits, vegetables, grains, use of GMOs vs non-GMO products, and the like.

Continuing in reference to FIG. 2, reduction model 234 training data may include a plurality of data entries including nutrient identities (e.g., nutrition elements), nutrient amounts (e.g., nutrition facts from food, mg/kg nutraceuticals, phytonutrients, bioactive ingredients, microbial populations, and the like), wherein the data entries are associated with effects on colonization of pathogens. Such training data may include nutrient amounts that prevent attachment and colonization of the gut epithelial by pathogens, foods that improve mucous and glycan production by epithelial cells, nutrients that support IgA and IgG recruitment, for instance form Peyer's Patches, lymph, and the like Such training data may include nutrient amounts of a plurality of nutrients with proposed roles in infection such as zinc, calcium, and other minerals, water-soluble and fat-soluble vitamins, particular carbohydrates, and the like, wherein training data may relate nutrient amounts from in vivo and in vitro studies to effects on bacterial cell death, CFU/mL, or any effect on a pathogen.

Continuing in reference to FIG. 2, determining the at least a first nutrient amount 232 that aids in reduction of the at least a first microbe 218 may include determining the at least a first nutrient amount 232 as a function of the at least a first microbe 218 and the reduction model 234. Computing device 104 may accept an input of at least a first microbe 218 and output at least a first nutrient amount 232 intended to reduce the population and/or eventually eliminate the pathogen from the user's current microbial colonization state. Such an output of at least a first nutrient amount 232 may include a frequency and magnitude organized into a schedule for reducing the population and/or eliminating the pathogen from the microbiome profile 206. A "frequency," as used in this disclosure, is a number of consumption occurrences associated with a time course, such as daily, weekly, monthly, and the like, of which a nutrition element is intended to be consumed. Frequency may be determined as a function of the identified effect in microbe reduction strategy 216, wherein the frequency of consumption is tailored to provide a sufficient minimal nutrient level over a time A "magnitude," as used in this disclosure, is a serving size of at least a nutrition element as a function of the identified effect. Identifying the magnitude associated with the at least a nutrition element may include calculating a serving size of the at least a nutrition element as a function of the identified effect in the microbe reduction strategy 216. A nutrition element magnitude may include a calculated nutrient amount. Nutrient amounts may include dosages, for instance and without limitation, a particular dosage of NSAIDs (mg/kg), gluten (g/day), and the like Determining the at least a first nutrient amount 232 may include retrieving a nutrient amount from a database, such as a microbiome database described in further detail below. For instance, a plurality of nutrient amounts may be stored in a database wherein computing device 104 may look-up nutrient amounts as necessary.

Continuing in reference to FIG. 2, computing device 104 is configured to determine at least a first nutrition element 238, wherein the at least a first nutrition element 238 includes the at least a first nutrient amount 232. A "nutrition element," is an item that includes a nutrient intended to be used and/or consumed by user. A first nutrition element 238 may include consumed foods, medications, stimulants, supplements, probiotics, and the like that may contribute to eliminating a first microbe 218 and/or addressing a microbe indicator 204 from microbiome profile 206 (e.g., symptom).

Continuing in reference to FIG. 2, identifying a first nutrition element 238 may include training a machine-learning process with training data, wherein training data includes a plurality of data entries that correlates a plurality of nutrient amounts to a plurality of nutrition elements. Machine-learning process may include any machine-learning process, algorithm, and/or model described herein, as performed by a machine-learning module described in further detail below. Machine-learning process may derive relationships in nutrient amounts that relate to particular nutrition elements, provided that nutrition elements may contain nutrients that aid promoting the pathogen's colonization of the user. For instance and without limitation, nutrients amounts may include nutrients to promote growth of competing organisms, reduce the pathogen population; however, foods with a first nutrient amount 232 may contain nutrients that work antagonistically. Training a machine-learning process may generate a function (or series of functions) which "learn" which nutrition elements work toward eliminating a first microbe 218. Such training data may include nutrition facts of nutrition elements as it relates to promoting or suppressing growth of a variety of microorganisms. Training data may include a plurality of data entries that correlates nutrient amounts and their associated effects to microbe category 210. Such training data may include vitamin and mineral amounts to address particular bacterial infections. A machine-learning model trained with such data may "learn" to output a first nutrition element 238 as a function of input (first nutrient amount 232). Such training data may originate from any source as described herein, such as from a database, web browser and the Internet, the user, wearable device, a physician, medical history, biological extraction test result, and the like.

Continuing in reference to FIG. 2, identifying a first nutrition element 238 may include calculating the at least a nutrient amount as a function of the microbe category 210 of the user. Calculating a nutrient amount may include using a trained machine-learning process to automatically calculate nutrient amounts (e.g., mg kg, mg cal, mg/g macromolecule, and the like) as a function of the pathogen to be eliminated (input). Calculating nutrient amounts in this manner may include deriving functions, equations, and the like, from relationships observed in the training data between pathogen survivability and nutrients.

Continuing in reference to FIG. 2, computing device 104 may calculate a nutrient amount, for instance, by using a default amount, such as from a standard 2,000 calorie diet, and increasing and/or decreasing the amount according to a numerical scale as it relates to a pathogen (or beneficial microorganism). Such a calculation may include a mathematical operation such as subtraction, addition, multiplication, and the like; alternatively, or additionally, such a calculation may involve deriving a loss function, vector analysis, linear algebra, system of questions, and the like, depending on the granularity of the process. Nutrient amounts may include threshold values, or ranges or values, for instance and without limitation, derived from classified of subsets of users, as described above. Nutrient amounts may be calculated as heat maps (or similar mathematical arrangements), for instance using banding, where each datum of microbiome profile 206 (e.g., pathogen to be eliminated) elicits a particular range of a particular nutrient amount or set of amounts. In non-limiting illustrative examples, such a calculation may include querying for and retrieving a standard amount of water-soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 2, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutrient amounts, for instance in a database. The amounts may be re-calculated and converted according to a user's microbiome profile 206. For instance, these amounts may relate to an average BMI, older male, classified to microbe category 210 indicating a particular pathogen to be eliminated, but may be adjusted according to unique user-specific microbe indicators 204. For example, an obese woman who has been placed on a strict 1,600 Calorie/day diet, curated according to identified risk factors (microbe indicators 204) may need the above amounts recalculated according to the calorie constraint (threshold), where some vitamin amounts may increase, some may decrease, and some may remain constant according to the pathogen to be eliminated.

Continuing in reference to FIG. 2, computing device 104 may identify the first nutrition element 238 by using a first nutrient amount 274 as an input and generating combinations, lists, or other aggregates of nutrition elements necessary to achieve nutrient amount. For instance, computing device 104 may use a template nutrient amount of '200 mg vitamin C' and build a catalogue of nutrition elements until the 200 mg vitamin C value is obtained. Computing device 104 may perform this task by querying for food items, for instance from a menu, grocery list, or the like, retrieving the vitamin C content, and subtracting the value from the nutrient amount. In non-limiting illustrative examples, computing device 104 may identify orange juice (90 mg vitamin C/serving; 200 mg-90 mg=110 mg) for breakfast, Brussel sprouts (50 mg vitamin C/serving; 110 mg-50 mg=60 mg)

for lunch, and baked potato (20 mg vitamin C/serving) and spicy lentil curry (40 mg vitamin C/serving; 60 mg−(20 mg+40 mg)=0 mg) for dinner. In such an example, computing device 104 may search according to a set of instructions including for instance and without imitation food preferences, allergies, restrictions, pathogen reduction, and the like, present in a microbiome profile 206, provided by a physician, user, or the like, and subtract each identified nutrition element from nutrient amount until a combination of nutrition elements that represents a solution is found. Once a solution is found, computing device 104 may generate a file of nutrition elements and store in a database, as described in further detail below.

Continuing in reference to FIG. 2, computing device 104 is configured to determine, using the microbe category 210 and the microbiome profile 206, a microbiome supplementation program. A "microbiome supplementation program," as used in this disclosure, is a strategy including at least a nutrient amount intended to be taken by the user to support the population of a microorganism. Supporting a population of a microorganism may include increasing the population of a microorganism until colonization is able to be established in user. Supporting a population of a microorganism may include introducing an exogenous microbial species to a user's microbiome. Supporting a population of a microorganism may include bolstering a population of a microorganism already found in and/or on a user. A microbiome supplementation program 240 may include a microorganism identifier such as the genus, species, and the like, a status including current level of microbe, the presence of microbe, incidence in user population, and the like, nutrient amounts and/or nutrition elements associated with supporting microbial populations.

Continuing in reference to FIG. 2, determining the microbiome supplementation program 240 includes identifying at least a second microbe to be included to the microbiome profile according to the classification. A "second microbe," as used in this disclosure, is at least one microorganism, microorganism type, and the like, that has been identified to be supplemented to microbiome profile 206 of a user. It is important to note that one may want to reduce the population and/or colonization of some microbes and increase others. For instance, *Clostridium* species, as a predominant cluster of commensal bacteria in the human gut, exert a wealth of salutary effects on intestinal homeostasis. *Clostridium* spp. have been long reported to attenuate inflammation and allergic diseases effectively owing to their distinctive biological activities. Their cellular components and metabolites, such as butyrate, secondary bile acids, and indole propionic acid, play a probiotic role primarily through energizing intestinal epithelial cells, strengthening intestinal barrier and interacting with immune system. In turn, dietary habits and physical state may shape unique patterns of *Clostridium* spp. in gut. In such an example, there may exist several *Clostridium* spp. that a user may wish to increase and/or supplement to their microbiome; however, some *Clostridium* spp. such as *C. difficile*, represent severe pathogens. The benefit *Clostridium* spp. pose to human gut flora may be achieved by supplementing certain microbial species, while reducing others, even within the same genus.

Continuing in reference to FIG. 2, identifying at least a second microbe 242 may include generating a balancing index, wherein generating the balancing index includes training a microbe balancing machine-learning model using a microbe balancing machine-learning process and training data which includes a plurality of data entries of microbiome profile data from subsets of users correlated to indexing values for identifying beneficial microbes. A "balancing index," as used in this disclosure, is a systematic index used to classify a microorganism as beneficial to a user's microbiome. Balancing index 244 may include a scoring index, repository, listing, and the like, of microbes (bacteria, protists, yeasts, and the like) that represent beneficial microorganisms for user. Beneficial microorganisms may be user-specific (one bacterial isolate may represent a benefit for a particular user, but a pathogen for another). Beneficial microorganisms may include probiotics part of a healthy user's microbiome (e.g., as indicated by microbe indicator 204 from a classification among a cohort of users). A microbe balancing machine-learning model 246 may include any machine-learning algorithm, model, or the like, as described herein. Microbe balancing machine-learning process 248 may include any machine-learning process, algorithm, and/or model, and the like, as performed by a machine-learning module as described in further detail below. Training data for training microbe balancing machine-learning model 246 may include training data as described above for pathogenicity machine-learning model 222. Training data may include, for instance and without limitation, microorganisms correlated to varying degrees of beneficial symbiotic relationships with users. Such relationships may include digestion, competition with opportunistic pathogens, among many others. Training data may include classified microbiome profiles 206, wherein microorganism identities are classified as a function of 1) microorganisms identified among healthy adults, and 2) microorganisms that have low pathogen index 220 scores. Training data may include microorganisms correlated to digestive ability for instance homo- and heterofermentative bacteria, xylose digestion, and the like. Training data may originate from any source descried herein such as a database, web browser and the Internet, peer-reviewed research database, physician, user input, and the like Such training data may be used to train microbe balancing machine-learning model 246 to derive a function, equation, or the like, from relationships observed in the training data, for instance and without limitation, that result in patterns of identification of novel beneficial microbial species as a function of their presence in cohorts of healthy adults.

Continuing in reference to FIG. 2, identifying at least a second microbe 242 may include generating a balancing standard, wherein generating the balancing standard may include training a microbe balancing classifier using a balancing classification machine-learning process and training data which includes a plurality of data entries of microbiome profile data from subsets of users correlated to microbe categories based on incidence of microbes. A "balancing standard," as used in this disclosure, is a microbiome reference that is used to measure microorganism benefit to user according to presence in microbiome. A balancing standard 250 may include a listing of microbiome organisms that may be found in a particular subset of users. A "particular subset of users" for a balancing standard 250 may include users that are alike or different from user, categorized based on sex, fitness level, diet, age, medical history, diagnoses, symptoms, among other categorizations based on microbe indicator 204, microbiome profile 206, microbe category 210, and the like. For instance, if user were diagnosed with a bacterial infection, overweight, diabetic, and the like, a subset of healthy users lacking bacterial infection, at healthy BMI, non-diabetic, and the like, may be used to generate a balancing standard 250 to compare against. In non-limiting illustrative examples, a subset of users to derive a balancing standard 250 for a microbiome profile indicating a user is diabetic may include classification among a cohort of users that have adjusted to diabetes but are otherwise healthy. This way, identification of isolates that may assist in disease management may be identified. Data relating to microbes present in users may be classified using balancing classifier 252. Balancing classifier 252 may include any machine-learning classifier, as described herein. Balancing classification machine-learning process 254 may include any machine-learning process, algorithm, and the like, as performed by machine-learning module described in further detail below. Training data for generating balancing classifier 252, for instance and without limitation, may include data that correlates symbiotic abilities of microorganisms with their colonization of the human gut; in this way, bacterial isolates may be classified according to digestive capabilities, protection against pathogens, association with disease states, and the like.

Continuing in reference to FIG. 2, identifying at least a second microbe 242 may include determining a balancing threshold from the balancing standard 250. A "balancing threshold," as used in this disclosure, is a cutoff threshold determined from the balancing index 244 and the balancing standard 250 for identifying beneficial microorganisms. For instance and without limitation, balancing threshold may include a numerical value, function of values, mathematical expression, and the like which indicates a value, above which a microorganism may be identified as a beneficial microbe that represents a second microbe 242 to be supplemented to user's microbiome profile 206. In non-limiting illustrative examples, balancing threshold may include a tiered numerical value system, wherein balancing threshold dictates that microbes with balancing index <20 are not very beneficial and >75 should be part of a user's microbiome. Balancing threshold may be determined from balancing classifier 252 according to observations about the incidence rate of microbes in health cohorts.

Continuing in reference to FIG. 2, generating the balancing index 244 may include assigning the balancing index 244 to each element in the microbiome profile 212 of the user. Microbiome profile 212 may have associated with each datum (e.g., microorganism species) a pathogen index 220 and/or balancing index 244. For instance, a high balancing index score may indicate a highly beneficial microorganism that may be missing from user microbiome, or a microorganism found in user microbiome that is highly correlated among healthy adults. Assigning balancing index 244 may be performed as described above for pathogen index 220.

Continuing in reference to FIG. 2, identifying at least a second microbe 242 may include comparing the microbiome profile 206 of the user to the balancing standard generated by the microbe balancing classifier 252. Balancing threshold may be generated as a function of the balancing standard 250 and the balancing classifier 252. Computing device 104 may compare microbiome profile 206 and balancing threshold to identify microorganisms that correlate to ameliorating a current symptom in the user (e.g., lactose intolerance, dry skin, and the like) and/or represent organisms highly correlated among target cohorts. Target cohorts may be healthy adults, adults with a target BMI value, a target visceral fat content, daily caloric intake targets, and the like that is a user is targeting to improve health state. Computing device 104 may compare microbiome profile 206 (balancing indexed) and balancing threshold by comparing the strings (e.g., organism names) between lists to identify microbes that are above a threshold value but are currently absent from user, wherein organisms will be added to microbiome supplementation program 240. Computing device 104 may compare a balancing-indexed microbiome profile 206 to balancing threshold, to identify potentially beneficial microorganisms that are currently present. A "balancing indexed microbiome profile," as used in this disclosure, is a microbiome profile 206 of a user that has been indexed according to balancing index 244 for comparing to balancing threshold. For instance, if an organism exists in microbiome profile 206 that does not match balancing standard 256, then computing device may derive a solution according to scoring criteria derived from the balancing index 244 and the balancing threshold.

Continuing in reference to FIG. 2, identifying the at least a second microbe 242 may include identifying the at least a second microbe 242 as a function of the comparison. Computing device 104 may compare microbiome profile 206 and balancing standard by determining a balancing threshold value. For instance and without limitation the comparison may include a threshold numerical value, above which a microorganism is identified as beneficial. In such an instance, a threshold value may be derived from the balancing classifier 252, wherein the index values are derived, and microbiomes are classified according to prevalence among a cohort of users (e.g., among healthy adults, and the like).

Continuing in reference to FIG. 2, determining a microbiome supplementation program 240 includes determining at least a second nutrient amount that aids in supplementation to microbiome profile of the at least a second microbe 242. A "second nutrient amount," as used in this disclosure, is a quantity of a nutrient amount intended to increase, support, and/or introduce the population of a second microbe 242. A second nutrient amount 256 may include a mass amount of a vitamin, mineral, macronutrient (carbohydrate, protein, fat), a numerical value of calories, mass amounts of phytonutrients, antioxidants, bioactive ingredients, nutraceuticals, and the like. A second nutrient amount 256 may include a food item, beverage, and/or supplement (e.g., probiotic) intended to introduce a new microorganism into the microbiome of user. Determining at least a second nutrient amount 256 may include retrieving a nutrient amount from a database, such as a microbiome database described in further detail below. For instance, a plurality of nutrient amounts may be stored in a database wherein computing device 104 may look-up nutrient amounts as necessary.

Continuing in reference to FIG. 2, determining the at least a second nutrient amount 256 that aids in supplementation of the at least a second microbe 242 may include training a supplementation model using a supplementation machine-learning process and training data, wherein training data includes a plurality of data entries of nutrition amounts correlated to effects on increasing microbial populations. Supplementation model 258 may include any machine-learning algorithm, model, and the like, as described herein. Supplementation machine-learning process 260 may include any machine-learning process, algorithm, or the like, as described herein and/or performed by a machine-learning module as described in further detail below. Supplementation model 258 training data may include any trading data described herein for machine-learning process, algorithms, and/or models. Training data may originate from any source described herein. In non-limiting illustrative examples, supplementation model 258 training data may include nutrient amounts, nutrition elements, beverages, probiotics, supplements, and the like, correlated with supporting introduction, growth, and/or colonization of a plurality of beneficial microorganisms.

Continuing in reference to FIG. 2, computing device 104 may determine the at least a second nutrient amount 256 as a function of the at least a second microbe 242 and the supplementation model 258. Training data may be used to generate supplementation model 258, which may be trained to derive an equation, function, and the like, that describes relationships observed in the training data for nutrient amounts as it relates to supporting beneficial bacterial species, fungi, protists, amoeba, and the like. Computing device may accept an input of a second microbe 242 and, as a function of the supplementation model 258, output the at least a second nutrient amount 256 that may promote the introduction, growth, and/or colonization of the second microbe 242. Supplementation model 258 may be used to determine a nutrient amount that works synergistically to bolster beneficial species and aid in reduction of pathogenic species, as described above.

Continuing in reference to FIG. 2, determining microbiome supplementation program 240 includes identifying at least a second nutrition element, wherein of the at least a second nutrition element includes the at least a second nutrient amount. A second nutrition element 262 may include consumed foods, medications, stimulants, supplements, probiotics, and the like that may contribute to supporting supplementation of a second microbe 242 to microbiome profile 206. A second nutrition element 262 may be determined in any manner as described herein for first nutrition element 238.

Continuing in reference to FIG. 2, computing device 104 is configured to generate a microbiome balance plan, using the microbe reduction strategy 216 and the microbiome supplementation program 240, wherein the microbiome balance plan includes a frequency and a magnitude for establishing balanced colonization in the user. A "microbiome balance plan," as used in this disclosure, includes dietary recommendations (nutrient amounts, nutrition elements, and the like) intended to balance microbiome profile 206. "Balancing" microbiome profile 206 may include eliminating pathogens, supplementing beneficial microorganisms, and/or combinations thereof. Microbiome balance plan 264 may include a frequency (timing of meals, supplements, and the like) and a magnitude (serving size, nutrient amount, and the like) for establishing balanced colonization in the user. This may include a variety of scheduling paradigms according to how many live organisms, spores, eggs, and the like, of an organism must be introduced to sustain colonization. For instance, introduction may need to be tiered with smaller amounts first being introduced, and gradually increased daily. Once colonization is established with beneficial microorganisms and pathogens have been eliminated, continued exposure of the microorganism may not be necessary. In such a case, relationships observed between nutrient amounts, nutrition elements, and pathogens and/or beneficial isolates, as determined by machine-learning models described herein, may be utilized to accurately define microbiome balance plan 264 terms and conditions.

Continuing in reference to FIG. 2, generating the microbiome balance plan 264 may include generating an objective function with the at least a first nutrition element 238 and the at least a second nutrition element 262 wherein the objection function outputs at least an ordering of a plurality of nutrition elements according to constraints from the microbe reduction strategy 216 and the microbiome supplementation program 240. An "objective function," as used in this disclosure, is a mathematical function that may be used by computing device 104 to score each possible combination of nutrition elements, wherein the objective function may refer to any mathematical optimization (mathematical programming) to select the 'best' element from a set of available alternatives. Selecting the 'best' element from a set of available alternatives may include a combination of nutrition elements which achieves the nutrient amounts in addressing microbe reduction strategy 216, microbiome supplementation program 240, microbiome profile 206 in a user.

Continuing in reference to FIG. 2, in non-limiting illustrative examples, an objective function may include performing a greedy algorithm process. A "greedy algorithm" is defined as an algorithm that selects locally optimal choices, which may or may not generate a globally optimal solution. For instance, computing device 104 may select combinations of nutrition elements so that values associated therewith are the best value for each category. For instance, in non-limiting illustrative example, optimization may determine the combination of the most efficacious 'serving size', 'timing of consumption', 'probiotic product', 'phytonutrient', and the like, categories to provide a combination that may include several locally optimal solutions but, together, may or may not be globally optimal in combination.

Still referring to FIG. 2, in further non-limiting illustrative examples, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user (e.g., lactose intolerance, poor absorption, food allergy, and the like), and a linear program may use a linear objective function to calculate ingredient combinations, considering how these limitations effect combinations. In various embodiments, system 100 may determine a set of instructions towards building microbiome balance plan 264 that maximizes a total bacterial infection prevention score subject to a constraint that there are other competing objectives. Such a score may include a summation of pathogen index 220 and balance index 244 for each element in microbiome profile 206, wherein "maximizing" the score may be performed according to the numerical scale, and what criteria is used for "high" and "low" scores. For instance, if achieving one nutrient amount and a second nutrient amount may result in needing to select a first nutrition element and a second nutrition element, wherein each may compete in balancing microbiome (e.g., adopting two or more diet types simultaneously may not be feasible, boosting beneficial microbe that boosts pathogen may not be feasible, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 2, in further non-limiting illustrative examples, objective function may include minimizing a loss function, where a "loss function" is an expression of an output which a process minimizes to generate an optimal result. For instance, achieving a first nutrient amount 238 and a second nutrient amount 256 may be set to a nominal value, such as '100', wherein the objective function selects elements in combination that reduce the value to '0', wherein the nutrient amounts are '100% achieved'. In such an example, 'maximizing' would be selecting the combination of nutrition elements that results in achieving nutrient amounts by minimizing the difference, where suboptimal pairing results in score increases. As a non-limiting example, computing device 104 may assign variables relating to a set of parameters, which may correspond to microbiome balance plan 264 components, calculate an output from a mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Figure 3:
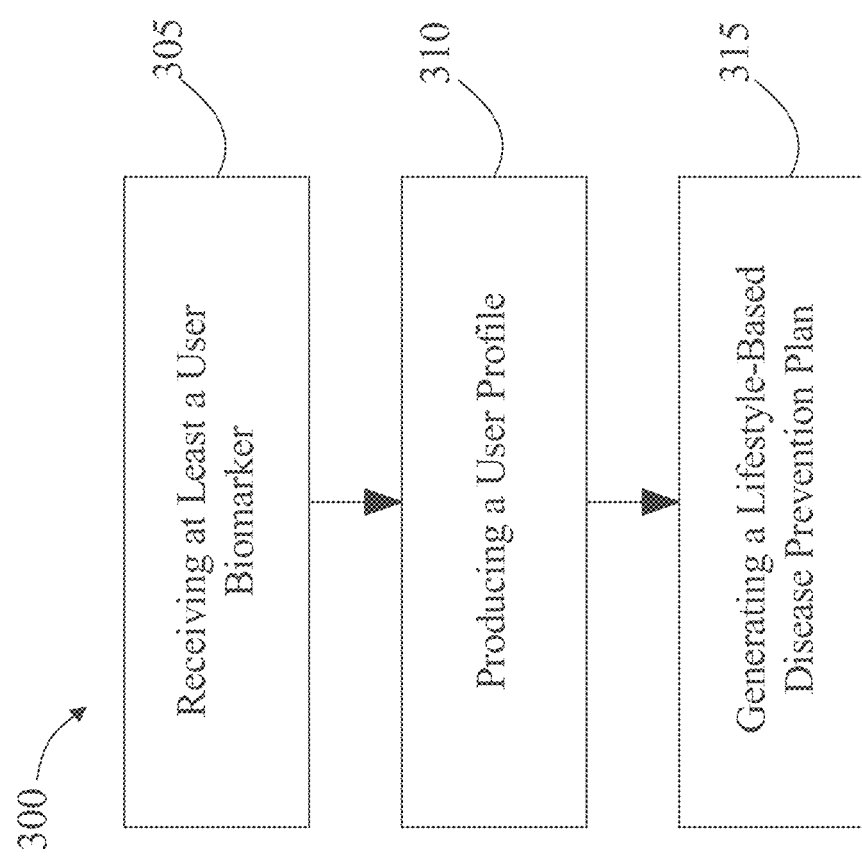
FIG. 3 is a block diagram illustrating a method for generating a lifestyle-based disease prevention plan.

Now referring to FIG. 3, an exemplary embodiment of a method 200 for lifestyle-based disease prevention plan is illustrated. At step 305, method 300 includes receiving, by a computing device 104, at least a user biomarker input 108.

Still referring to FIG. 3, at step 310, method 300 includes producing, by the computing device 104, a user profile, where producing the user profile includes determining a user identifier as a function of the user biomarker, generating at least a query as a function of the user identifier, extracting at least a textual output as a function of the at least a query, and producing the user profile as a function of the at least a textual output.

Continuing to refer to FIG. 3, at step 315, method 300 includes generating, by the computing device 104, a lifestyle-based disease prevention plan as a function of the user profile, where generating the lifestyle-based disease prevention plan includes training a machine learning process with a lifestyle training data set wherein the lifestyle training data set further comprises a plurality of inputs containing lifestyle elements correlated to a plurality of outputs containing diseases prevented and producing the lifestyle-based disease prevention plan as a function of the user profile and the machine learning process.

Figure 4:
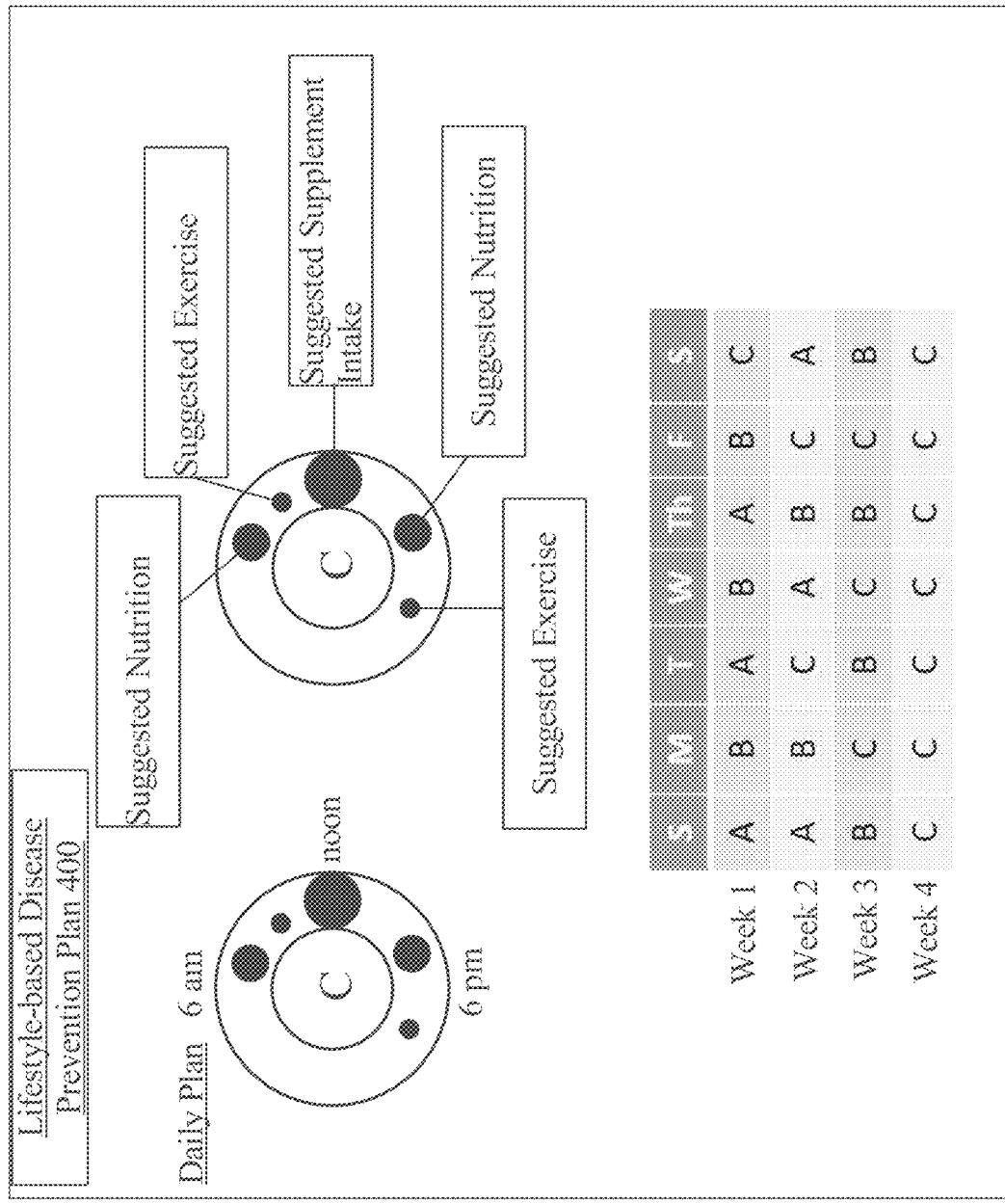
FIG. 4 is a diagrammatic representation of a lifestyle-based disease prevention plan.

Now referring to FIG. 4, an exemplary embodiment of a lifestyle-based disease prevention plan 400 is illustrated. Lifestyle-based disease prevention plan 400 may include a schedule for arranging nutrition elements, according to for instance a 24-hour timetable, as designated on the left, where consumption is planned along a user's typical day-night cycle, beginning at ~6 am until just after 6 pm. Nutrition element may include breakfast (denoted as mid-sized dark grey circle), which may correspond to a file of breakfast-related first nutrition element 138 (denoted b1, b2, b3, b4 . . . bn, to the nth breakfast item). Nutrition element may include a first subset of snacks eaten throughout the day to, for instance supplementing beneficial organisms missing from microbiome, such as probiotics, (denoted as small black circles), which may correspond to a file of snacking-related second nutrition element (denoted s2, s4, s6, s8 . . . sn, to the nth snacking item). Nutrition element may include dinner (denoted as large-sized light grey circle), which may correspond to a file of dinner-related nutrition elements (denoted d1, d2, d3, d4 . . . dn, to the nth dinner item). Lifestyle-based disease prevention plan 400 may include a variety of diets, as denoted in the monthly schedule at the bottom, Sunday through Saturday. Lifestyle-based disease prevention plan 400 'C' is shown, which may be an idealistic goal for user to achieve by the end of the month, where reduction-based plans 'A' and supplementation-based plans 'B' are intermediate plans intended to guide user to the 'balanced' microbiome. Nutrition elements classified by 'meal type' may be further modified by 'A' and 'B' according to user preferences collected by computing device 104 throughout the process. Circle sizes, denoting nutrition element classes may relate to portion sizes (magnitude), which are graphed along the circle corresponding to the timeline (frequency) they are expected to be consumed. User may indicate which nutrition element from each category was consumed, and when it was consumed, to arrive at an adherence score, as described in further detail below.

Figure 5:
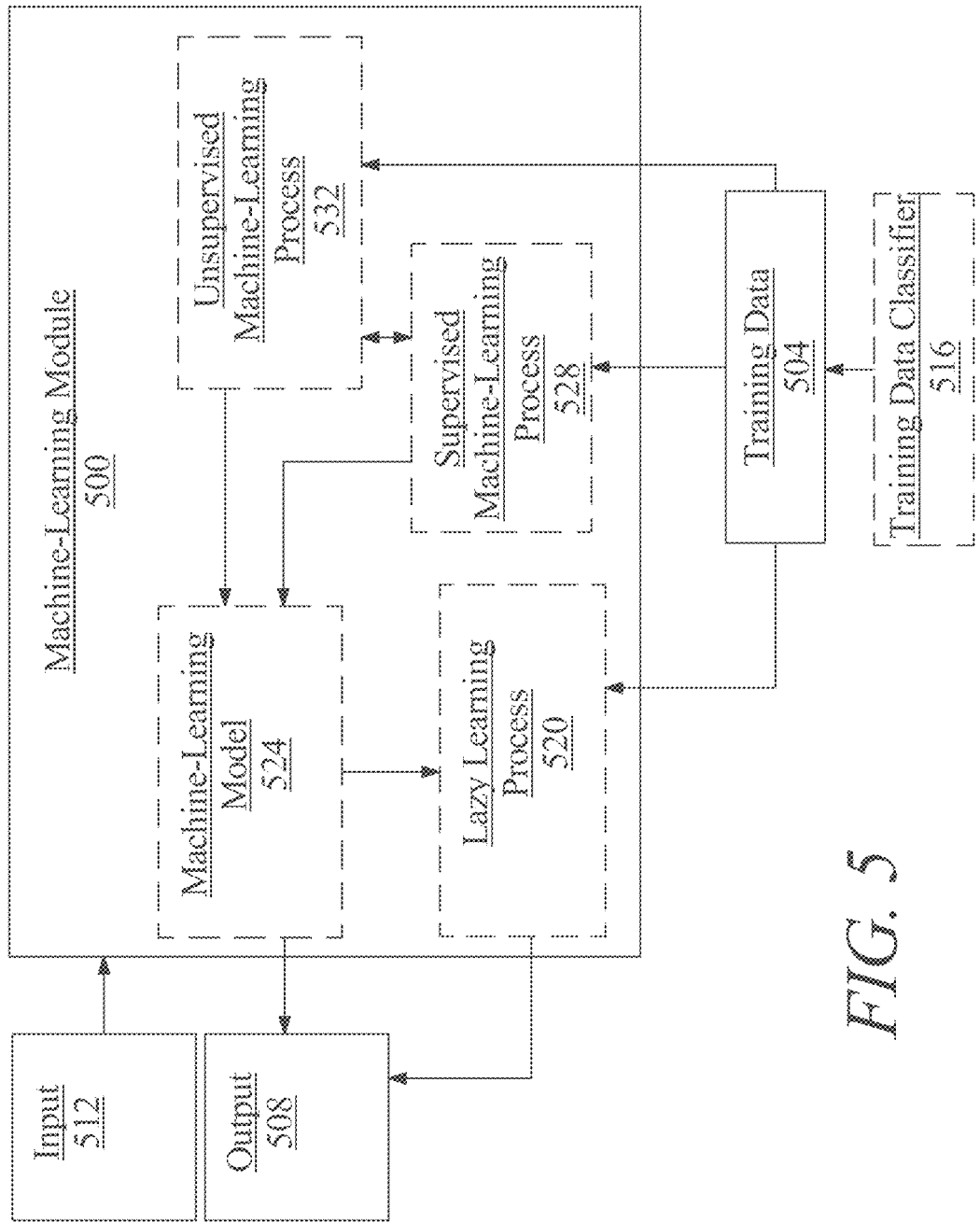
FIG. 5 is an exemplary diagram of a machine learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example flight elements and/or pilot signals may be inputs, wherein an output may be an autonomous function.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to sub-categories of flight elements such as torques, forces, thrusts, directions, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors' algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include flight elements and/or pilot signals as described above as inputs, autonomous functions as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
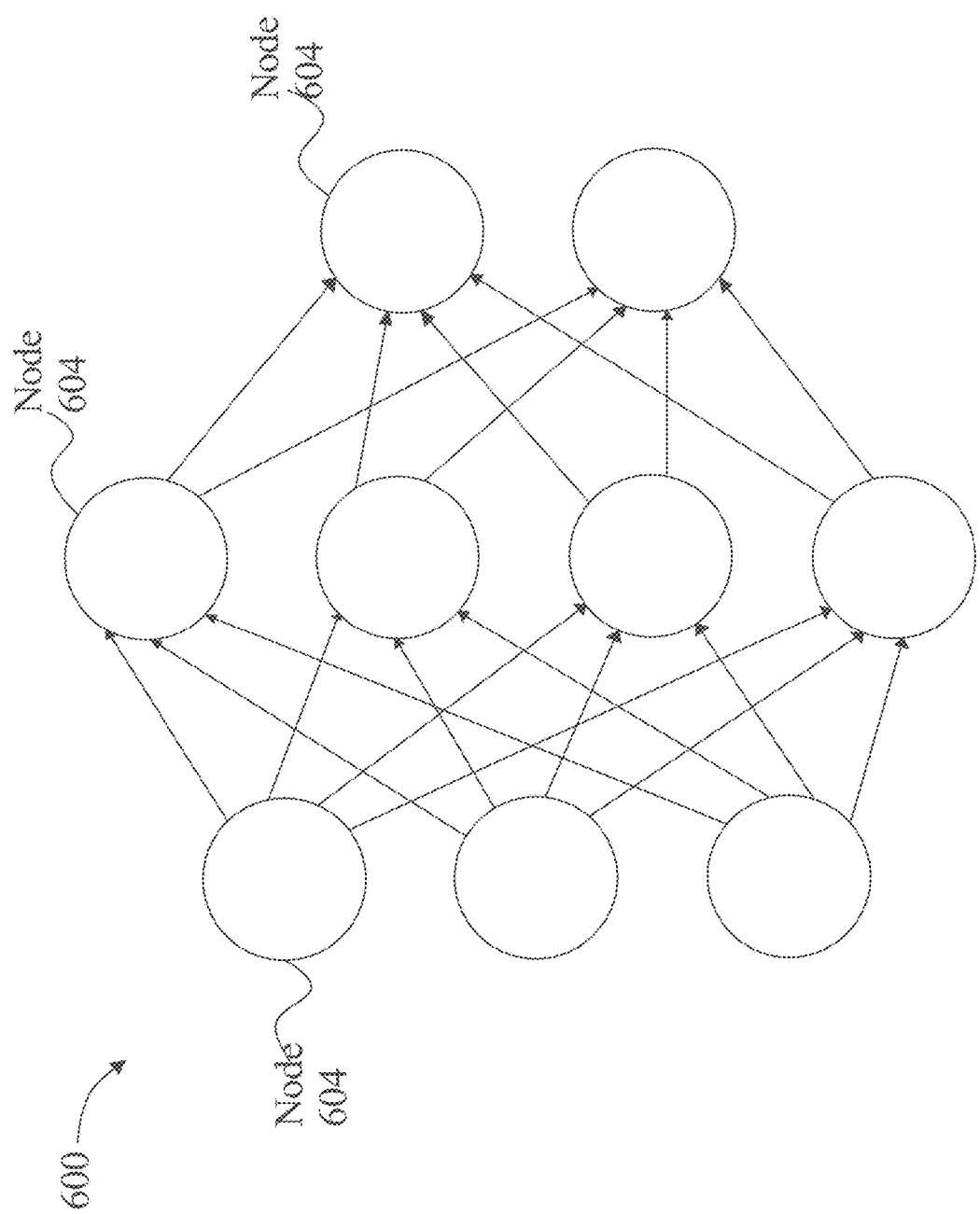
FIG. 6 is an exemplary embodiment of a neural network.

Referring now to FIG. 6, an exemplary embodiment of neural network 600 is illustrated. A neural network also known as an artificial neural network, is a network of "nodes," or data structures having one or more inputs, one or more outputs, and a function determining outputs based on inputs. Such nodes 604 may be organized in a network, such as without limitation a convolutional neural network, including an input layer of nodes 604, one or more intermediate layers, and an output layer of nodes 604. Connections between nodes 604 may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Figure 7:
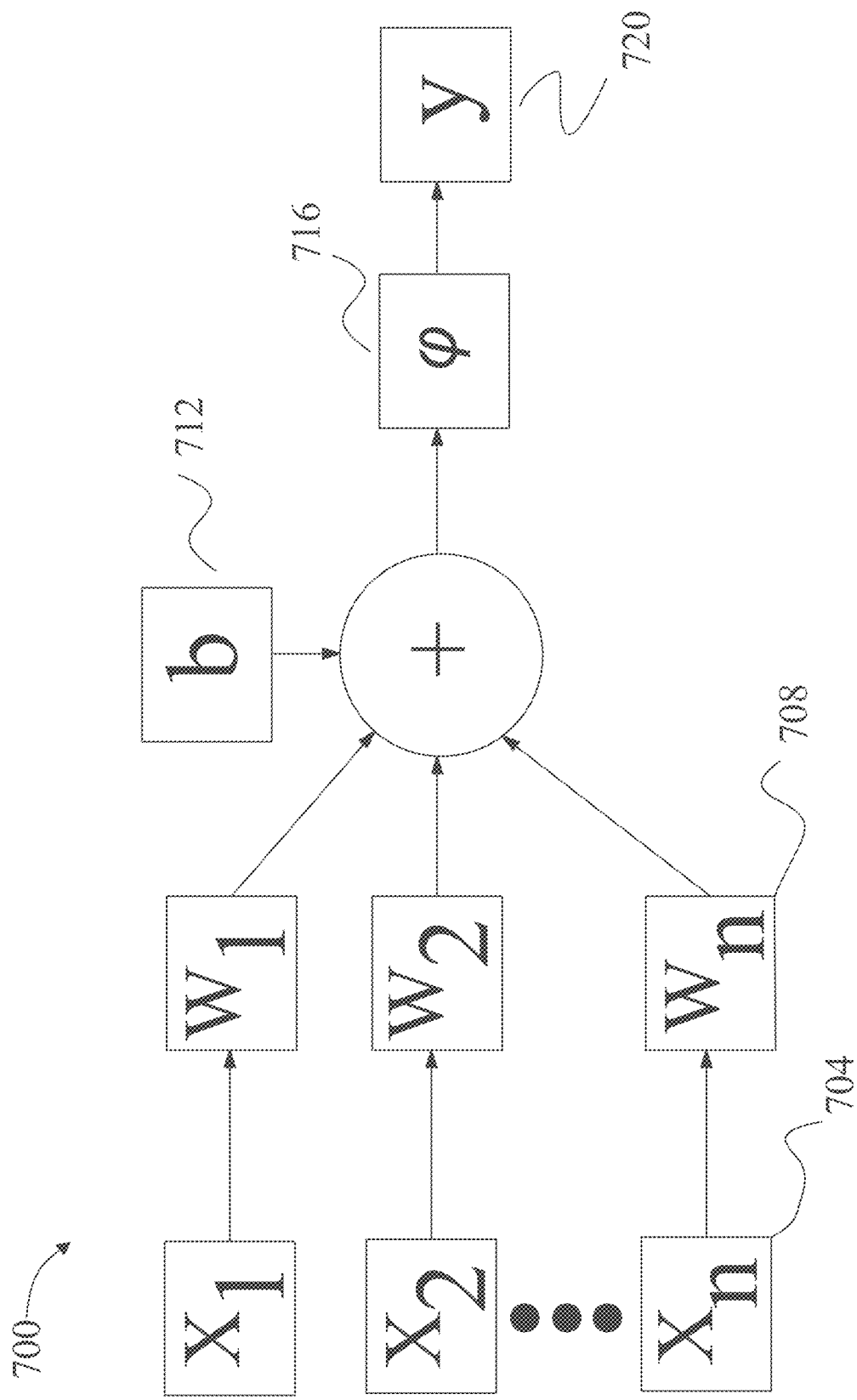
FIG. 7 is an exemplary representation of a neural network node.

Referring now to FIG. 7, an exemplary embodiment of a node 700 of a neural network 600 is illustrated. A node may include, without limitation a plurality of inputs $x_n$ 704 that may receive numerical values from inputs to a neural network containing the node and/or from other nodes. Node may perform a weighted sum of inputs using weights $w_n$ 708 that are multiplied by respective inputs $x_n$ 704. Additionally or alternatively, a bias b 712 may be added to the weighted sum of the inputs such that an offset is added to each unit in the neural network layer that is independent of the input to the layer. The weighted sum may then be input into a function p 716, which may generate one or more outputs y 720. Weight $w_n$ 708 applied to an input $x_n$ 704 may indicate whether the input is "excitatory," indicating that it has strong influence on the one or more outputs y, for instance by the corresponding weight having a large numerical value, and/or a "inhibitory," indicating it has a weak effect influence on the one more inputs y 720, for instance by the corresponding weight having a small numerical value. The values of weights $w_n$ 708 may be determined by training a neural network using training data, which may be performed using any suitable process as described above. In an embodiment, and without limitation, a neural network may receive semantic units as inputs and output vectors representing such semantic units according to weights $w_n$ that are derived using machine-learning processes as described in this disclosure.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
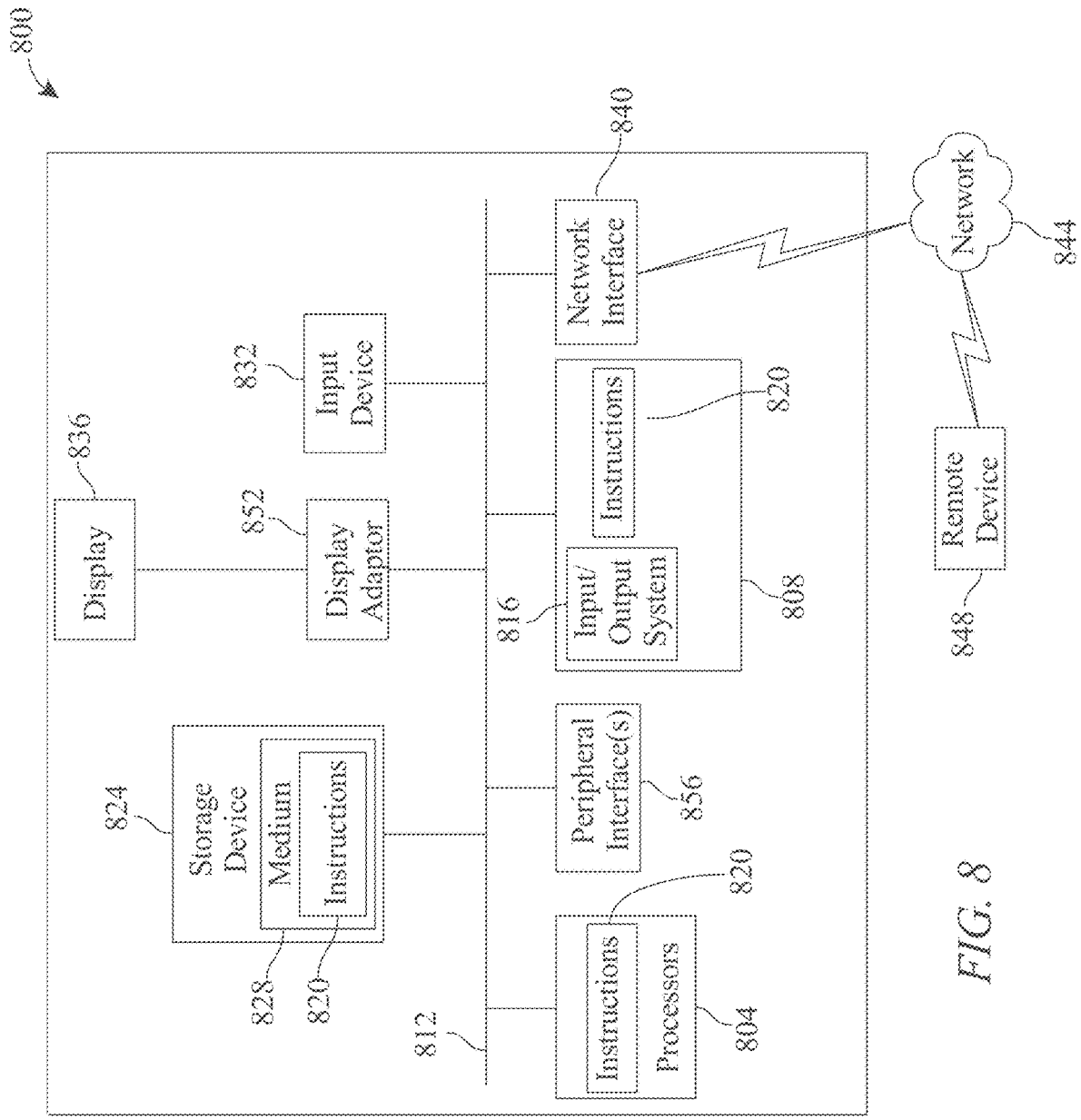
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a lifestyle-based disease prevention plan, the system comprising a computing device configured to:
   receive at least a user biomarker input;
   produce a user profile as a function of the at least a user biomarker input, wherein producing the user profile comprises:
      determining a user identifier as a function of the at least a user biomarker input;
      generating at least a query as a function of the user identifier, wherein generating at least a query comprises a parsing module configured to convert the at least a query into a second form of the at least a query, wherein the parsing module further comprises a language processing module configured to perform at least a dependency parsing process;
      extracting at least a textual output as a function of the at least a query; and
      producing the user profile as a function of the at least a textual output; and
   generate a lifestyle-based disease prevention plan as a function of the user profile, wherein the lifestyle-based disease prevention plan comprises a consumption schedule for nutritional elements, wherein generating the lifestyle-based disease prevention plan comprises:
      training a machine learning process with a lifestyle training data set, wherein the lifestyle training data set further comprises a plurality of inputs containing lifestyle elements correlated to a plurality of outputs containing diseases prevented, wherein training the machine learning process comprises:
         updating the lifestyle training data set as a function of inputs and outputs of a previous iteration of the machine learning process; and
         retraining the machine learning process using the updated lifestyle training data; and
      producing the lifestyle-based disease prevention plan as a function of the user profile using the trained machine learning process.

2. The system of claim 1, wherein the computing device is further configured to:
   receive a user input relating to the lifestyle-based disease prevention plan; and
   calculate a user compliance with the lifestyle-based disease prevention plan.

3. The system of claim 2, wherein the user input is received from a wearable device.

4. The system of claim 2, wherein the computing device is further configured to send user reminders related to the lifestyle plan.

5. The system of claim 1, wherein training the machine learning process with the lifestyle data training set comprises utilizing a neural network.

6. The system of claim 1, wherein the computing device is further configured to generate a user lifestyle compliance dataset.

7. The system of claim 6, wherein the computing device is further configured to transmit a lifestyle plan comparison set to a user device as a function of the lifestyle compliance dataset.

8. The system of claim 1, wherein the computing device is further configured to calculate a likeability of a user to follow the lifestyle plan as a function of the machine learning process.

9. The system of claim 1, wherein the computing device is further configured to transmit a user lifestyle plan reminder.

10. The system of claim 9, wherein a transmission of the user lifestyle plan reminder includes attributes readable by an AI assistant software.

11. A method for generating a lifestyle-based disease prevention plan, the method comprising;
  receiving, by a computing device, at least a user biomarker input;
  producing, by the computing device, a user profile as a function of the at least a user biomarker input, wherein producing the user profile comprises:
    determining a user identifier as a function of the at least a user biomarker input;
    generating at least a query as a function of the user identifier, wherein generating at least a query comprises a parsing module configured to convert the at least a query into a second form of the at least a query, wherein the parsing module further comprises a language processing module configured to perform at least a dependency parsing process;
    extracting at least a textual output as a function of the at least a query; and
    producing the user profile as a function of the at least a textual output; and
  generating, by the computing device, a lifestyle-based disease prevention plan as a function of the user profile, wherein the lifestyle-based disease prevention plan comprises a consumption schedule for nutritional elements, wherein generating the lifestyle-based disease prevention plan comprises:
    training a machine learning process with a lifestyle training data set, wherein the lifestyle training data set further comprises a plurality of inputs containing lifestyle elements correlated to a plurality of outputs containing diseases prevented, wherein training the machine learning process comprises:
      updating the lifestyle training data set as a function of inputs and outputs of a previous iteration of the machine learning process; and
      retraining the machine learning process using the updated lifestyle training data; and
    producing the lifestyle-based disease prevention plan as a function of the user profile and the machine learning process.

12. The method of claim 11, wherein method further comprises:
  receiving, by the computing device, a user input relating to the lifestyle-based disease prevention plan; and
  calculating, by the computing device, a user compliance with the lifestyle-based disease prevention plan.

13. The method of claim 12, wherein receiving the user input comprises utilizing a wearable device.

14. The method of claim 12, wherein the method further comprises sending, by the computing device, user reminders related to the lifestyle plan.

15. The method of claim 11, wherein training the machine learning process with the lifestyle training data set comprises utilizing a neural network.

16. The method of claim 11, wherein the method further comprises generating, by the computing device, a user lifestyle compliance dataset.

17. The method of claim 16, wherein the method further comprises transmitting, by the computing device, a lifestyle plan comparison set to a user device as a function of the lifestyle compliance dataset.

18. The method of claim 11, wherein the method further comprises calculating, by the computing device, a likeability of a user to follow the lifestyle plan as a function of the machine learning process.

19. The method of claim 11, wherein the method further comprises transmitting, by the computing device, a user lifestyle plan reminder.

20. The method of claim 19, wherein transmitting the user lifestyle plan reminder comprises attributes readable by an AI assistant software.

* * * * *